US012672844B2

(12) United States Patent
Viswanath et al.

(10) Patent No.: US 12,672,844 B2
(45) Date of Patent: Jul. 7, 2026

(54) ULTRASOUND COEXISTENCE IN A MULTI TRANSDUCER FETAL MONITORING SYSTEM

(71) Applicant: GE Precision Healthcare LLC, Waukesha, WI (US)

(72) Inventors: Shrihari Viswanath, Bangalore (IN); Rajendra Naik, Bangalore (IN); Benoy Abraham, Bangalore (IN)

(73) Assignee: GE Precision Healthcare LLC, Waukesha, WI (US)

( * ) Notice: Subject to any disclaimer, the term of this patent is extended or adjusted under 35 U.S.C. 154(b) by 88 days.

(21) Appl. No.: 18/426,977

(22) Filed: Jan. 30, 2024

(65) Prior Publication Data

US 2025/0241617 A1     Jul. 31, 2025

(51) Int. Cl.
*A61B 8/08*          (2006.01)
*A61B 8/00*          (2006.01)
*B06B 1/02*          (2006.01)
*B06B 1/06*          (2006.01)

(52) U.S. Cl.
CPC .......... *A61B 8/0866* (2013.01); *A61B 8/4483* (2013.01); *B06B 1/0215* (2013.01); *B06B 1/0614* (2013.01); *B06B 2201/40* (2013.01); *B06B 2201/76* (2013.01)

(58) Field of Classification Search
None
See application file for complete search history.

(56) References Cited

U.S. PATENT DOCUMENTS

| | | | |
|---|---|---|---|
| 5,088,497 | A | 2/1992 | Ikeda |
| 5,528,168 | A | 6/1996 | Kleveland |
| 6,288,577 | B1 | 9/2001 | Wong |

(Continued)

FOREIGN PATENT DOCUMENTS

| | | | |
|---|---|---|---|
| CN | 105342640 B | 2/2016 | |
| CN | 105913355 A | 8/2016 | |

(Continued)

OTHER PUBLICATIONS

Non-Final Office Action received for U.S. Appl. No. 18/426,572 dated May 5, 2025, 9 pages.

(Continued)

*Primary Examiner* — Jonathan D Armstrong
(74) *Attorney, Agent, or Firm* — Amin, Turocy & Watson, LLP

(57)          ABSTRACT

One or more systems, devices, computer-implemented methods and/or computer program products of use provided herein relate to ultrasound coexistence in an FMS. A system can comprise a memory that can store computer-executable components. The system can further comprise a processor that can execute the computer-executable components stored in the memory, wherein the computer-executable components can comprise a frequency generation component that can use a variable frequency generator circuitry to generate electronic signals at one or more different frequencies in at least one fetal sensor device (FSD) of a fetal monitoring system (FMS), wherein the electronic signals can cause a transducer of the at least one FSD to generate ultrasound signals at the one or more different frequencies.

20 Claims, 15 Drawing Sheets

(56)                    References Cited

U.S. PATENT DOCUMENTS

| 6,320,406 | B1 | 11/2001 | Morgan et al. | |
| 6,650,149 | B1 | 11/2003 | Wong | |
| 6,862,432 | B1 * | 3/2005 | Kim | H04B 1/18 |
| | | | | 455/193.1 |
| 6,963,249 | B2 * | 11/2005 | Devries | H03L 7/24 |
| | | | | 331/172 |
| 7,292,119 | B2 * | 11/2007 | Urakawa | H03L 7/099 |
| | | | | 331/11 |
| 7,949,444 | B2 | 5/2011 | Mukherjee | |
| 7,983,626 | B2 * | 7/2011 | Kim | H04B 1/18 |
| | | | | 455/193.1 |
| 8,055,887 | B2 | 11/2011 | Karstens | |
| 8,407,158 | B2 | 3/2013 | Suri et al. | |
| 8,696,578 | B2 | 4/2014 | Kabakov et al. | |
| 8,738,663 | B2 | 5/2014 | Gonzalez et al. | |
| 8,746,548 | B2 | 6/2014 | Terwilliger et al. | |
| 9,183,603 | B2 | 11/2015 | Borges et al. | |
| 9,396,037 | B2 | 7/2016 | Morsi et al. | |
| 9,536,044 | B2 | 1/2017 | White et al. | |
| 9,672,458 | B2 | 6/2017 | Burkhart et al. | |
| 9,734,448 | B2 | 8/2017 | Bolich | |
| 10,025,791 | B2 | 7/2018 | Lee | |
| 10,402,781 | B2 | 9/2019 | Terwilliger et al. | |
| 10,638,999 | B2 | 5/2020 | Shah | |
| 10,789,264 | B2 | 9/2020 | Crabtree et al. | |
| 10,810,390 | B2 | 10/2020 | Hegendoerfer et al. | |
| 10,901,834 | B2 | 1/2021 | Abhinav et al. | |
| 10,902,232 | B2 | 1/2021 | Peng | |
| 10,949,440 | B2 | 3/2021 | Schoueri et al. | |
| 11,087,878 | B2 | 8/2021 | Vesto et al. | |
| 11,240,181 | B1 | 2/2022 | Nagaraja et al. | |
| 11,309,060 | B2 | 4/2022 | Janevski et al. | |
| 11,321,338 | B2 | 5/2022 | Okorafor et al. | |
| 11,327,989 | B2 | 5/2022 | Wu et al. | |
| 11,451,201 | B1 * | 9/2022 | Hoffman | H03F 1/42 |
| 11,481,738 | B2 | 10/2022 | Tong et al. | |
| 11,599,729 | B2 | 3/2023 | Wu | |
| 11,842,188 | B2 | 12/2023 | Bregman et al. | |
| 2004/0036538 | A1 * | 2/2004 | Devries | H03B 5/1243 |
| | | | | 331/16 |
| 2004/0090265 | A1 | 5/2004 | Pradhan | |
| 2005/0130699 | A1 * | 6/2005 | Kim | H04B 1/0458 |
| | | | | 455/575.5 |
| 2005/0134491 | A1 * | 6/2005 | Huang | H03L 7/093 |
| | | | | 341/143 |
| 2005/0219003 | A1 * | 10/2005 | Urakawa | H03L 7/099 |
| | | | | 331/117 R |
| 2007/0243834 | A1 * | 10/2007 | Takei | H04B 1/1646 |
| | | | | 455/84 |
| 2007/0260155 | A1 * | 11/2007 | Rapoport | A61B 7/04 |
| | | | | 600/528 |
| 2008/0114249 | A1 | 5/2008 | Randall et al. | |
| 2009/0043203 | A1 | 2/2009 | Pelissier et al. | |
| 2010/0168596 | A1 | 7/2010 | Jaeschke et al. | |
| 2010/0191117 | A1 | 7/2010 | Kabakov | |
| 2010/0274145 | A1 | 10/2010 | Tupin, Jr. et al. | |
| 2010/0274750 | A1 | 10/2010 | Oltean et al. | |
| 2011/0160591 | A1 | 6/2011 | Smith et al. | |
| 2011/0254567 | A1 * | 10/2011 | Gehrig | G01N 33/365 |
| | | | | 324/663 |
| 2011/0295102 | A1 * | 12/2011 | Lakkis | A61B 5/02028 |
| | | | | 600/407 |
| 2012/0053465 | A1 | 3/2012 | Kudoh | |
| 2012/0123267 | A1 * | 5/2012 | Dow | A61B 8/483 |
| | | | | 600/443 |
| 2012/0232398 | A1 * | 9/2012 | Roham | A61B 8/565 |
| | | | | 600/528 |
| 2012/0286889 | A1 * | 11/2012 | Park | H03B 5/1268 |
| | | | | 331/117 FE |
| 2013/0087609 | A1 | 4/2013 | Nichol et al. | |
| 2013/0123637 | A1 | 5/2013 | Wohlschlager et al. | |
| 2013/0158407 | A1 | 6/2013 | Kabakov et al. | |
| 2013/0245436 | A1 | 9/2013 | Tupin, Jr. et al. | |
| 2014/0163378 | A1 | 6/2014 | Ohshima | |

| 2014/0276070 | A1 | 9/2014 | Kabakov et al. | |
| 2015/0146772 | A1 | 5/2015 | Fujimori | |
| 2015/0219580 | A1 * | 8/2015 | Gehrig | G01R 17/16 |
| | | | | 324/663 |
| 2015/0302176 | A1 | 10/2015 | Lyons et al. | |
| 2015/0372664 | A1 * | 12/2015 | Walker | H03B 9/14 |
| | | | | 331/49 |
| 2016/0204765 | A1 * | 7/2016 | Ferriss | H03J 5/0218 |
| | | | | 29/600 |
| 2017/0043189 | A1 * | 2/2017 | Stoddard | G10K 11/24 |
| 2017/0071579 | A1 | 3/2017 | Ko et al. | |
| 2017/0303899 | A1 | 10/2017 | Willsie | |
| 2018/0115197 | A1 * | 4/2018 | Li | H02J 50/80 |
| 2018/0317878 | A1 | 11/2018 | Wohlschlager et al. | |
| 2018/0338746 | A1 | 11/2018 | Wu et al. | |
| 2019/0019090 | A1 | 1/2019 | Chacko et al. | |
| 2019/0370671 | A1 | 12/2019 | Martinez Canedo et al. | |
| 2020/0261059 | A1 | 8/2020 | Xu et al. | |
| 2020/0365262 | A1 | 11/2020 | Sreenivasan et al. | |
| 2020/0380076 | A1 | 12/2020 | Taylor | |
| 2021/0064932 | A1 | 3/2021 | Wang et al. | |
| 2021/0241897 | A1 | 8/2021 | Casse et al. | |
| 2022/0005083 | A1 | 1/2022 | Patterson et al. | |
| 2022/0189618 | A1 | 6/2022 | Klassen et al. | |
| 2022/0192525 | A1 | 6/2022 | Franck et al. | |
| 2022/0233174 | A1 * | 7/2022 | Hwang | G01S 7/52096 |
| 2022/0265157 | A1 | 8/2022 | Charthad et al. | |
| 2022/0293246 | A1 | 9/2022 | Tweedie et al. | |
| 2022/0337189 | A1 * | 10/2022 | Huang | H03L 1/023 |
| 2022/0374300 | A1 | 11/2022 | Che et al. | |
| 2023/0034748 | A1 | 2/2023 | Bull et al. | |
| 2023/0168895 | A1 | 6/2023 | Shah et al. | |
| 2023/0238103 | A1 | 7/2023 | Murphy et al. | |
| 2023/0259821 | A1 | 8/2023 | Travalini et al. | |
| 2023/0335236 | A1 | 10/2023 | Dambman et al. | |
| 2023/0335238 | A1 | 10/2023 | Danckwardt | |
| 2023/0338000 | A1 | 10/2023 | B et al. | |
| 2024/0296352 | A1 | 9/2024 | Yanosy et al. | |
| 2025/0241615 | A1 * | 7/2025 | Naik | A61B 8/488 |

FOREIGN PATENT DOCUMENTS

| CN | 108231145 | A | 6/2018 |
| CN | 110035303 | A | 7/2019 |
| CN | 111899852 | A | 11/2020 |
| CN | 112364148 | A | 2/2021 |
| CN | 114073546 | A | 2/2022 |
| CN | 114118062 | A | 3/2022 |
| CN | 114882979 | A | 8/2022 |
| CN | 114898848 | A | 8/2022 |
| CN | 115098673 | A | 9/2022 |
| CN | 115964460 | A | 4/2023 |
| CN | 114446423 | B | 6/2023 |
| WO | 2020/167316 | A1 | 8/2020 |
| WO | 2022206822 | A1 | 10/2022 |
| WO | 2022/229088 | A1 | 11/2022 |
| WO | 2023/088983 | A1 | 5/2023 |

OTHER PUBLICATIONS

"Direct Digital Synthesis Based Ultrasound Doppler Transducer ED—Darl Kuhn", ip.com, ip.com Inc., West Henrietta, NY, US, Jan. 18, 2013 (Jan. 18, 2013), XP013155646, ISSN: 1533-0001.

EP application 25150330.6 filed Jan. 6, 2025—extended Search Report issued Jul. 2, 2025; 14 pages.

Extended European Search Report received for European Patent Application Serial No. 25150797.6 dated Jun. 2, 2025, 11 pages.

Non-Final office action received for U.S. Appl. No. 18/422,591 dated Dec. 20, 2024, 42 pages.

Deloitte, "Tech Trends 2021", Deloitte Insights, https://www2. deloitte.com/content/dam/insights/articles/7023_TT-machine-data-revolution-feeding-the-machine/DI_2021-TT-machine-data-revolution. pdf, Last accessed Nov. 2, 2023, 21 pages.

(56)       References Cited

OTHER PUBLICATIONS

Anadiotis, George, "5 Technology Trends for the Roaring 20s, Part 2: AI, Knowledge Graphs, Infinity and Beyond", On-line publication on ZDNET, https://www.zdnet.com/article/5-technology-trends-for-the-roaring-20s-part-2-aiknowledge-graphs-infinity-and-beyond/, Jan. 16, 2020, 9 pages.

McMahan et al., "Federated Learning: Collaborative Machine Learning without Centralized Training Data", Google Blog, https://ai.googleblog.com/2017/04/federated-learning-collaborative.html, Apr. 6, 2017, 5 pages.

Tensorflow, "TensorFlow Federated: Machine Learning on Decentralized Data", Online Available at URL: https://www.tensorflow.org/federated, Last accessed Aug. 28, 2023, 4 pages.

schema.org, Company website https://schema.org/, Last accessed Aug. 28, 2023, 1 page.

schema.org, "IoT and Schema.org: Getting Started", https://schema.org/docs/iot-gettingstarted.html, Last accessed Sep. 19, 2023, 15 pages.

Maguire et al., "A Metadata-Based Architecture for User-Centered Data Accountability", Electron Markets, Online available at https://link.springer.com/article/10.1007/s12525-015-0184-z, vol. 25, 2015, pp. 155-160.

Chavarukattil et al., "Generative Artificial Intelligence Driven Self-Healing Agent for Medical Devices", U.S. Appl. No. 18/749,679, filed Jun. 21, 2024, 37 pages.

Extended European Search Report received for European Patent Application Serial No. 25150798.4 dated Jun. 16, 2025, 7 pages.

Notice of Allowance received for U.S. Appl. No. 18/426,572 dated Nov. 19, 2025, 8 pages.

Anonymously, "Dual Ultrasound Switching Using Analog Switches", IPCOM000239085D, Oct. 10, 2014, 5 pages.

Docker, M. F., "Doppler Ultrasound Monitoring Technology", British Journal of Obstetrics and Gynaecology, vol. 100, No. 9, Mar. 1993, pp. 18-20.

Non-Final office action received for U.S. Appl. No. 18/426,544 dated Mar. 13, 2026, 20 pages.

* cited by examiner

100

SYSTEM

PROCESSOR 102

106

MEMORY 104

FREQUENCY GENERATION COMPONENT 108

STORAGE COMPONENT 110

SEPARATION COMPONENT 112

SIGNAL PROCESSING COMPONENT 114

SYNCHRONIZATION COMPONENT 116

FREQUENCIES 118

500

600
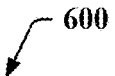
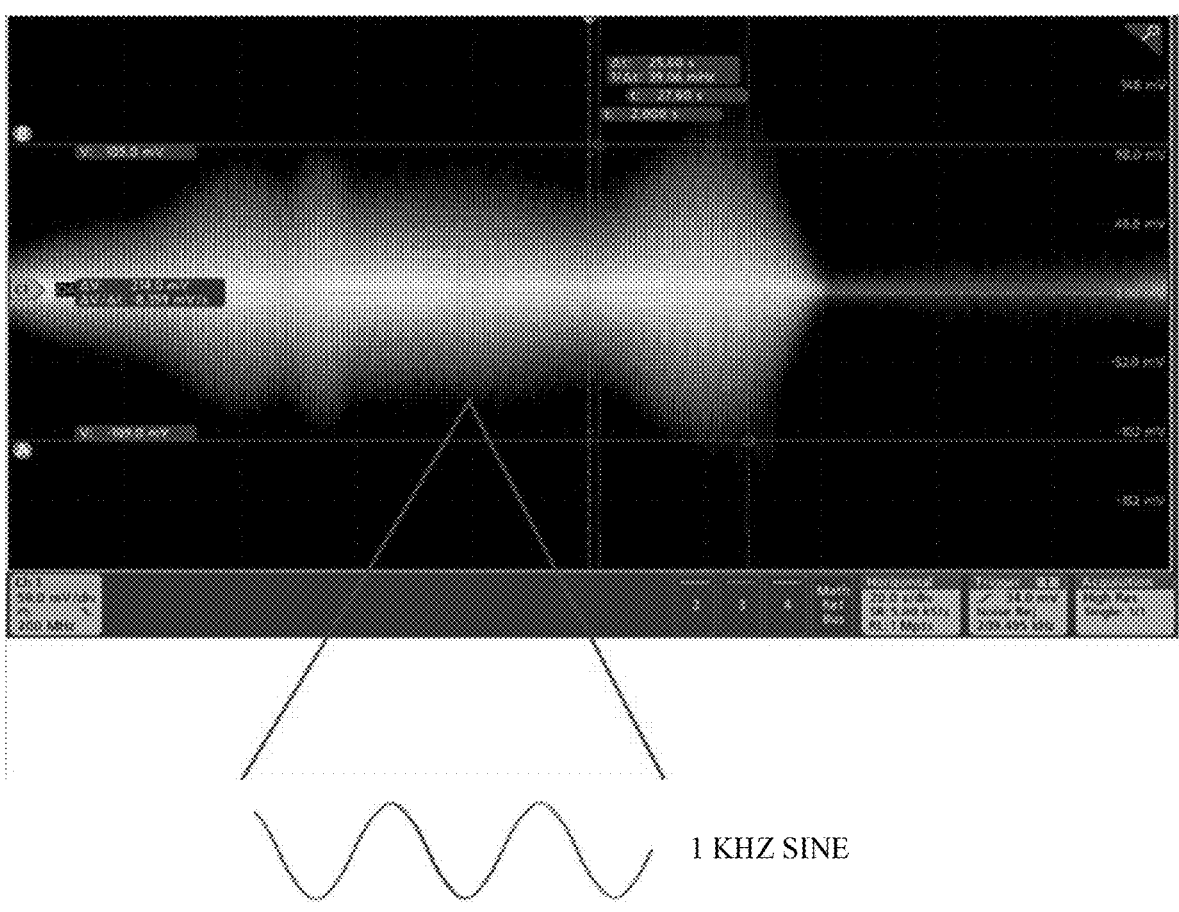
1 KHZ SINE
FIG. 6

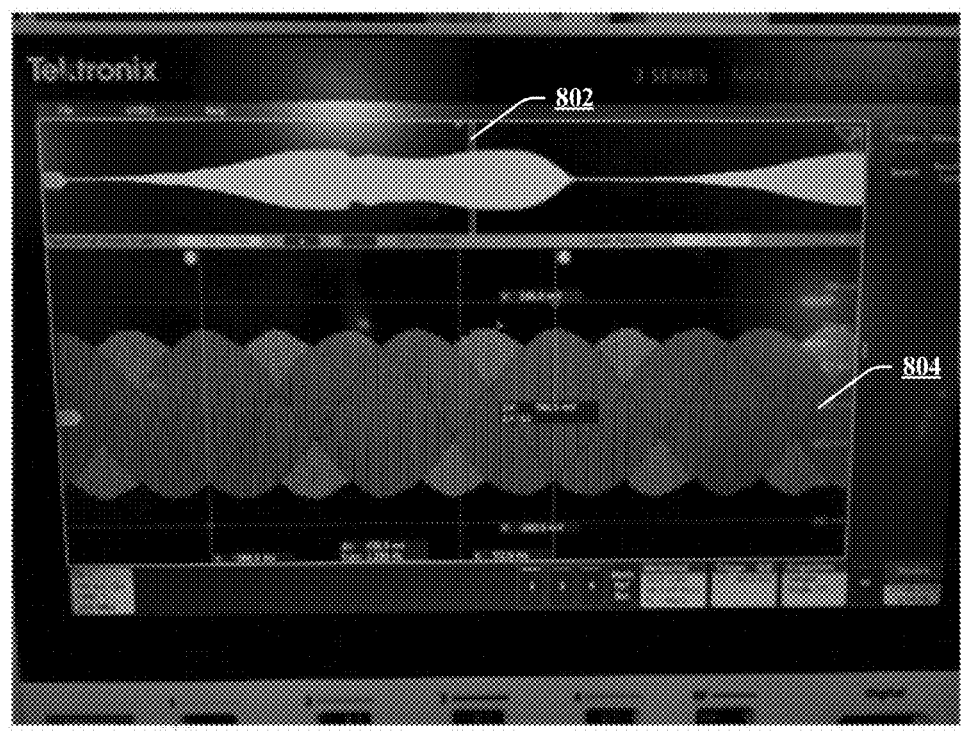
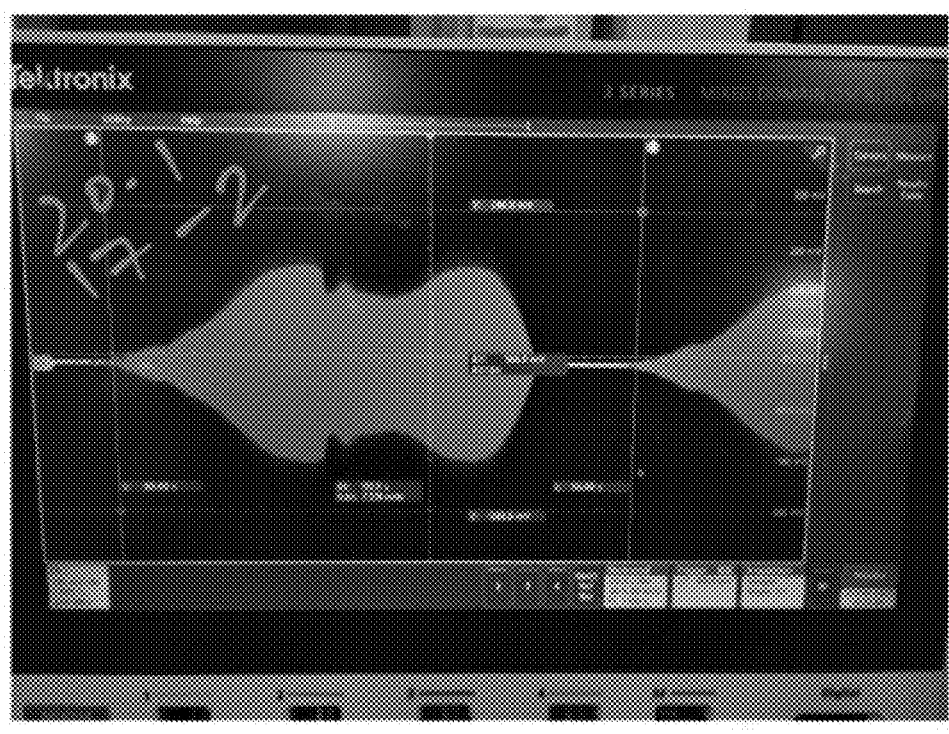
FIG. 8

1100
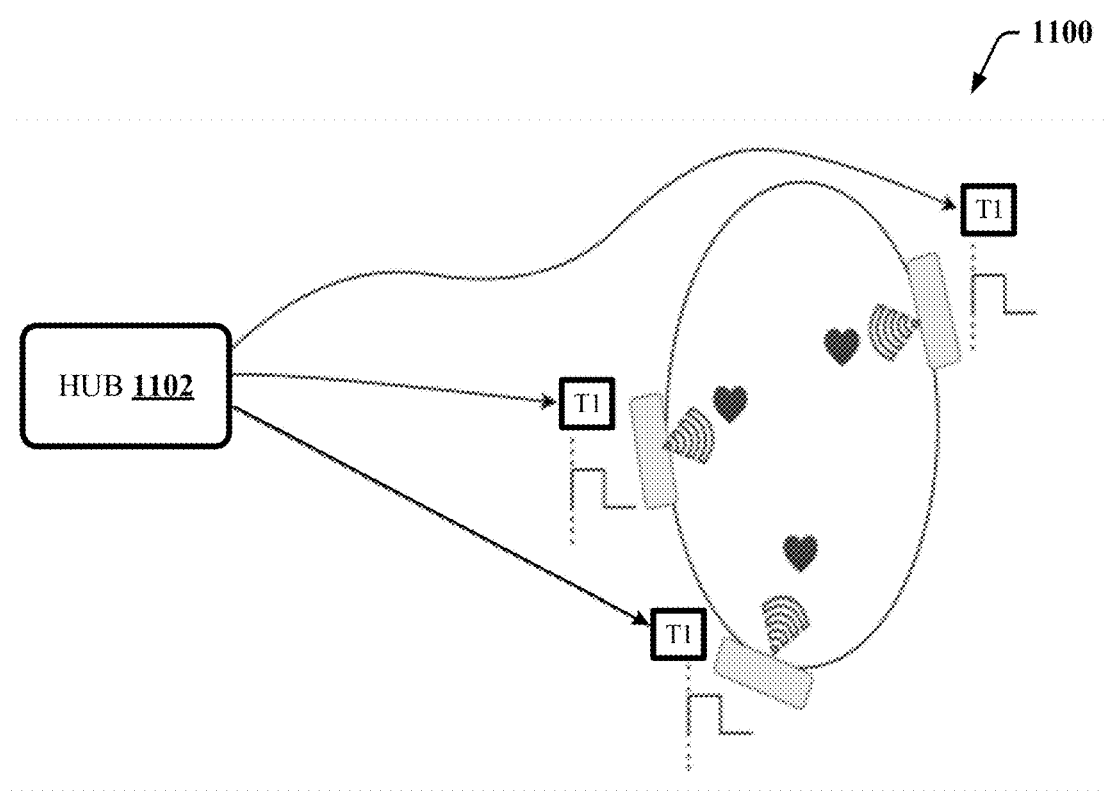
1120
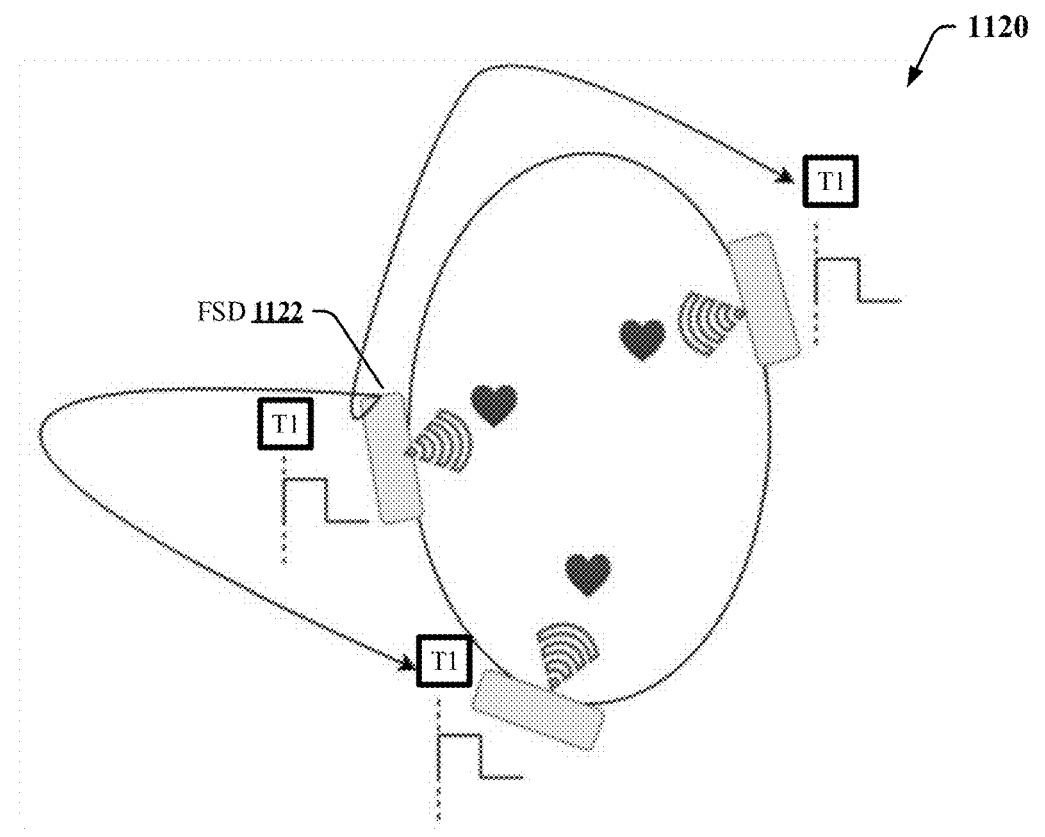
FIG. 11

1300 ⌐

1302

Generating, by a device operatively coupled to a processor, using a variable frequency generator circuitry, electronic signals at one or more different frequencies in at least one fetal sensor device (FSD) of a fetal monitoring system (FMS), wherein the at least one FSD dynamically adjusts a transmit voltage of the at least one FSD to maintain one acoustic power value at the one or more different frequencies

1304

Separating, by the device, respective carrier frequencies of the plurality of FSDs in the FMS such that a frequency difference between carrier frequencies of any two FSDs is not a multiple of a PRR of either FSD, wherein separating the respective carrier frequencies of the plurality of FSDs generates predictable harmonics during crosstalk in the FMS

1306

Implementing, by the device, an automatic gain control stage and a filter to selectively eliminate the predictable harmonics to eliminate crosstalk in the FMS, wherein the automatic gain control stage is implemented as a software, a hardware or a combination of the software and the hardware

1308

Performing, by the device, a periodic PRR synchronization to synchronize a start of a transmit period of the at least one FSD with respective starts of transmit periods of one or more additional FSDs in the FMS to prevent ultrasound signals generated by the at least one FSD from becoming demodulated by respective carrier frequencies generated by the one or more additional FSDs in the FMS

1310

Performing, by the device, a pulse phase synchronization using a control system to prevent a signal transmitted by a first FSD of the FMS from entering a receive period of a second FSD of the FMS located directly across the first FSD at a distance, wherein the control system measures an amount of harmonics generated by the first FSD at the second FSD and gradually shifts a phase of the signal transmitted by the first FSD to align the signal transmitted by the first FSD with a signal transmitted by the second FSD in the FMS

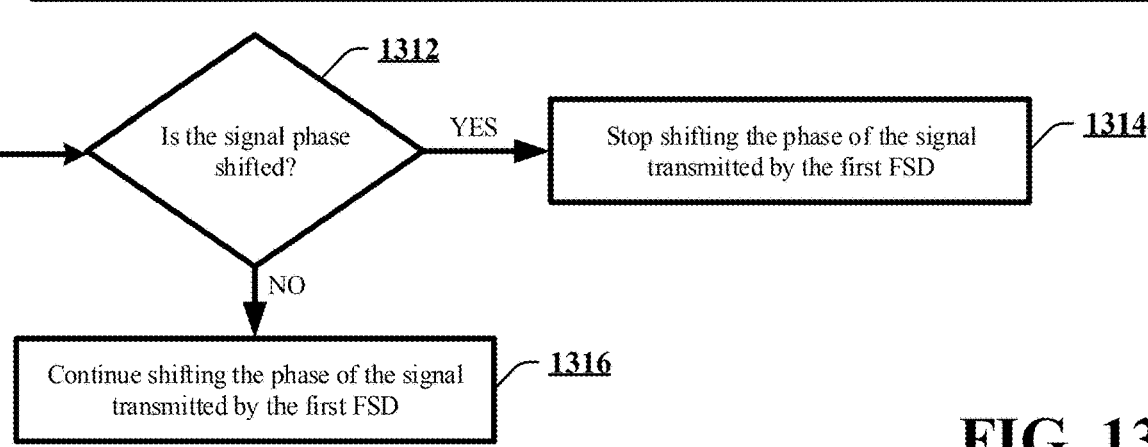

1312

Is the signal phase shifted?

YES → Stop shifting the phase of the signal transmitted by the first FSD   1314

NO

Continue shifting the phase of the signal transmitted by the first FSD   1316

FIG. 13

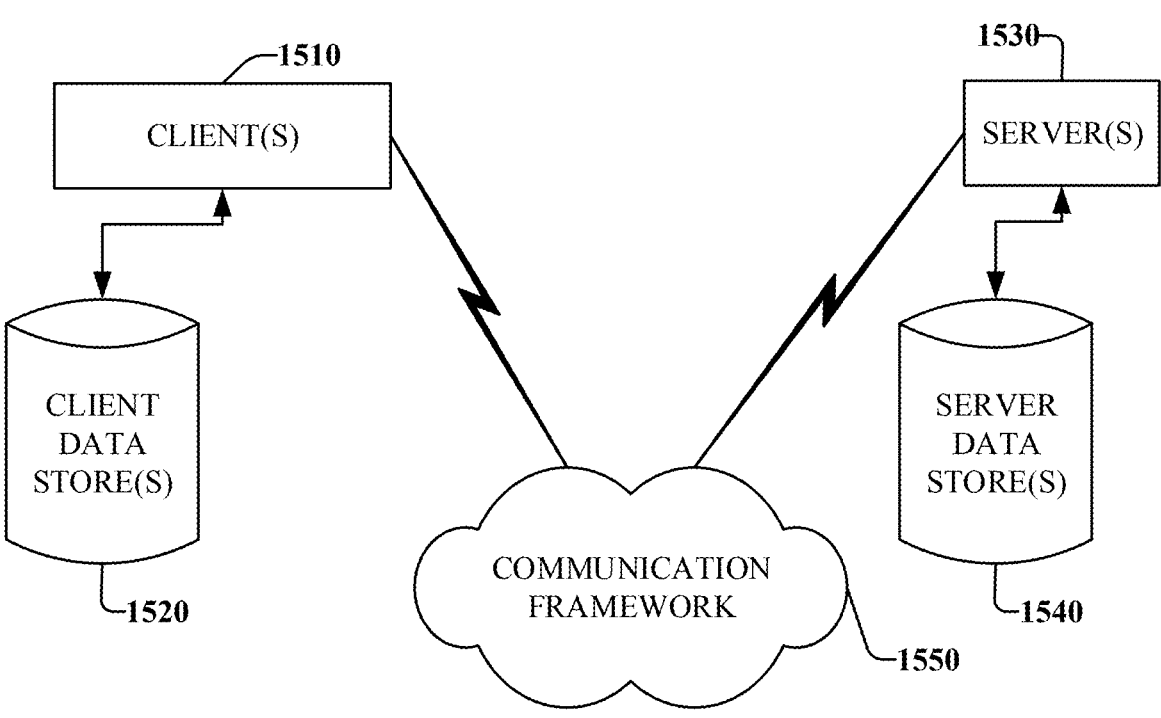
FIG. 15

ULTRASOUND COEXISTENCE IN A MULTI TRANSDUCER FETAL MONITORING SYSTEM

TECHNICAL FIELD

The subject disclosure relates generally to ultrasound technology and, more specifically, to ultrasound coexistence in a fetal monitoring system (FMS) comprising one or more fetal sensor devices (FSDs).

BACKGROUND

Ultrasound sensors and transducers based on the doppler effect are used for detecting fetal heart rates (FHRs) and fetal movement, non-stress tests in clinics and monitoring for fetal hypoxia or other situations where a fetus can be harmed, right before labor. Typically, an ultrasound transducer transmits an ultrasound carrier signal having a certain amplitude for a fixed time period, Tx, and the same transducer is then used to receive signals reflected from a fetus in a receive window, Rx, wherein the reflected signals are doppler shifted due to the movement of the heart tissues, fetal movements, etc. Using a demodulation technique, the ultrasound carrier signal can be stripped out and the doppler shift due to the movement of the heart tissues can be identified. Thereafter, correlation or peak detect algorithms are utilized to extract the fetal heart rate, fetal movement parameters, etc. from the signal and the signal is also morphed and driven to a speaker to generate a doppler audio output. In highly sensitive FMSs (e.g., multi FSD ultrasound systems) where multiple FSDs transmit pulses (ultrasound vibrations) into the same abdomen, interferences can occur between the FSDs, which can cause confusion between the hearts being monitored by each FSD. Avoiding such interferences can be crucial, especially for ensuring reliable and precise fetal monitoring. If all the FSDs operate at the same frequency, signal confusion can be caused between the FSDs (even for very small amplitudes). Separating frequencies in smart transducer systems (e.g., FMSs) can help overcome small signal confusion. However, crosstalk can still be caused due to Nyquist overlaps between the FSDs, inaccuracies in the frequencies being used for the pulse modulations/demodulations, and signal confusion due to aliasing and electronic interferences. Crosstalk is a phenomenon wherein signals transmitted by one FSD can interact with signals transmitted by another FSD resulting in generation of undesirable effects in a system. Given the high sensitivity of a transducer and the extremely high gains at the analog front end, harmonics can generally creep in and lead to repetitive waveforms that hoodwink the heart rate detection algorithm, which can lead to false interpretations of a Cardiotocograph (CTG).

Accordingly, systems or techniques for reliable ultrasound coexistence in an FMS can be desirable.

SUMMARY

The following presents a summary to provide a basic understanding of one or more embodiments described herein. This summary is not intended to identify key or critical elements, delineate scope of particular embodiments or scope of claims. Its sole purpose is to present concepts in a simplified form as a prelude to the more detailed description that is presented later. In one or more embodiments described herein, systems, computer-implemented methods, apparatus and/or computer program products that enable multiple FSD coexistence in an FMS are discussed.

According to an embodiment, a system is provided. The system can comprise a memory that can store computer-executable components. The system can further comprise a processor that can execute the computer-executable components stored in the memory, wherein the computer-executable components can comprise a frequency generation component that can use a variable frequency generator circuitry to generate electronic signals at one or more different frequencies in at least one FSD of an FMS, wherein the at least one FSD can dynamically adjust a transmit voltage of the at least one FSD to maintain one acoustic power value at the one or more different frequencies, wherein the at least one FSD can comprise a tunable inductor-capacitor (LC) tank circuit comprising large capacitance varactors that can tune a resonant frequency of the tunable LC tank circuit to a carrier frequency of the at least one FSD, wherein tuning the resonant frequency of the tunable LC tank circuit to the carrier frequency of the at least one FSD can comprise using a digital-to-analog converter (DAC) to adjust biasing voltages of a balanced varactor network, and wherein the carrier frequency can be a frequency selected from the one or more different frequencies.

In an aspect of the aforementioned system, the electronic signals can cause a transducer of the at least one FSD to generate ultrasound signals at the one or more different frequencies, and adjusting the biasing voltages of the balanced varactor network can dynamically change a capacitance value of the large capacitance varactors.

In one or more embodiments of the aforementioned system, a storage component can store a DAC value corresponding to maximizing gain of the tunable LC tank circuit at the carrier frequency of the at least one FSD. In one or more embodiments of the aforementioned system, the variable frequency generator circuitry can use an attenuated shifted frequency to automate a calibration process for the tunable LC tank circuit, and wherein the at least one FSD can be calibrated to maximize gain at the carrier frequency of the at least one FSD. In one or more embodiments of the aforementioned system, tuning the resonant frequency of the tunable LC tank circuit to the carrier frequency of the at least one FSD can improve reception sensitivity and gain of the tunable LC tank circuit at the carrier frequency, desensitize the at least one FSD to respective carrier frequencies of additional FSDs in the FMS, and characterize and compensate for a behavior of the resonant frequency of the tunable LC tank circuit resulting from temperature fluctuations experienced by the at least one FSD to cause the tunable LC tank circuit to exhibit a consistent performance despite the temperature fluctuations.

In one or more embodiments of the aforementioned system, a separation component can separate respective carrier frequencies of the plurality of FSDs in the FMS such that a frequency difference between carrier frequencies of any two FSDs is not a multiple of a pulse repetition rate (PRR) of either FSD, wherein separating the respective carrier frequencies of the plurality of FSDs can generate predictable harmonics during crosstalk in the FMS. In one or more embodiments of the aforementioned system, a signal processing component can implement an automatic gain control (AGC) stage and a filter to selectively eliminate the predictable harmonics to eliminate crosstalk in the FMS, wherein the automatic gain control stage can be implemented as a software, a hardware or a combination of the software and the hardware.

In one or more embodiments of the aforementioned system, a synchronization component can perform a periodic PRR synchronization to synchronize a start of a transmit period of the at least one FSD with respective starts of transmit periods of one or more additional FSDs in the FMS to prevent ultrasound signals generated by the at least one FSD from becoming demodulated by respective carrier frequencies generated by the one or more additional FSDs in the FMS. In one or more embodiments of the aforementioned system, the periodic PRR synchronization can be performed by using a monitor that can send signals in real time to FSDs of the FMS or by using a main FSD to transmit signals to additional FSDs in the FMS, and the periodic PRR synchronization can be performed wirelessly or through wired connections.

In one or more embodiments of the aforementioned system, the synchronization component can perform a pulse phase synchronization using a control system to prevent a signal transmitted by a first FSD of the FMS from entering a receive period of a second FSD of the FMS located directly across the first FSD at a distance, wherein the control system can measure an amount of harmonics generated by the first FSD at the second FSD and gradually shift a phase of the signal transmitted by the first FSD to align the signal transmitted by the first FSD with a signal transmitted by the second FSD in the FMS.

According to various embodiments, the above-described system can be implemented as a computer-implemented method or as a computer program product.

BRIEF DESCRIPTION OF THE DRAWINGS

One or more embodiments are described below in the Detailed Description section with reference to the following drawings:

FIG. 6 illustrates a diagram of an example, non-limiting interference pattern representative of crosstalk artefacts in accordance with one or more embodiments described herein.

FIG. 8 illustrates diagrams of example, non-limiting interference patterns representative of crosstalk artefacts in accordance with one or more embodiments described herein.

FIG. 11 illustrates diagrams of example, non-limiting scenarios showing a synchronization of pulse patterns generated by FSDs positioned on a pregnant woman for monitoring fetal parameters (heartbeats of triplets or gross body movement) in accordance with one or more embodiments described herein.

FIG. 13 illustrates a flow diagram of an example, non-limiting method that can enable multiple FSD coexistence in an FMS in accordance with one or more embodiments described herein.

FIG. 15 illustrates an example networking environment operable to execute various implementations described herein.

DETAILED DESCRIPTION

Figure 1:
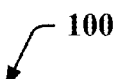
FIG. 1 illustrates a block diagram of an example, non-limiting system that can enable multiple FSD coexistence in an FMS in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

In highly sensitive multi FSD ultrasound systems where multiple FSDs can transmit pulses (ultrasound waves) into the abdomen of a mother, there can be interferences between the FSDs, resulting in confusion related to fetal hearts being monitored by each FSD. Avoiding the interferences can ensure reliable and precise fetal monitoring. While Time division multiplexing (TDM) can be implemented for ensuring multiple FSD coexistence, the FSDs can only operate in succession in TDM, wherein one FSD can transmit a signal and immediately receive a reflected signal, in pre-assigned time slots, followed by another FSD transmitting and receiving signals, and so on. That is, in TDM, FSDs can transmit and receive pulses one at a time and in succession. TDM can cause lower resolution during sampling which can lead to lower signal-to-noise ratios (SNRs) and a reduction of a sensing range (depth). If all the FSDs operate at the same frequency without TDM, signal confusion can be caused between the FSD (even for very small amplitudes of received reflected signals). Separating frequencies using Frequency Domain Multiplexing/Frequency Division Multiplexing (FDM) in smart transducer systems (e.g., FMSs) can help overcome small signal confusion. However, crosstalk can still be caused due to Nyquist overlaps between FSDs, inaccuracies in one or more of the frequencies being used for the pulse modulations or demodulations, and signal confusion due to aliasing and electronic interferences. As described earlier, crosstalk is a phenomenon wherein signals transmitted by one FSD can interact with signals transmitted by another FSD resulting in generation of undesirable effects in a system. Given the high sensitivity of an FSD and extremely high gains at the analog front end, harmonics can generally creep in, which can lead to repetitive waveforms that can hoodwink a heart rate detection algorithm and lead to false interpretations of a CTG. In existing fetal monitoring techniques, all FSDs of an FMS operate at a single frequency. That is, existing FMSs do not include multiple FSDs operating at different frequencies. Further, in existing FMSs, a single FSD cannot operate at multiple frequencies, and such existing systems find it challenging to have one sensor that can be configurable to multiple frequencies. Thus, reliable techniques for generating multiple frequencies using a single FSD and for eliminating crosstalk for ultrasound coexistence in an FMS can be desirable.

Various embodiments herein can provide solutions to one or more of the problems described above in connection with interference between multiple FSDs, wherein one FSD can detect a signal that is the reflected ultrasound signal of another FSD during fetal monitoring. In various embodiments, each FSD of an FMS can be tuned for different resonant frequencies of an LC network and a corresponding DAC value can be stored in the FSD. An LC circuit (also known as an LC filter or LC network) can be defined as an electrical circuit consisting of passive circuit elements including an inductor (L) connected to a capacitor (C). The LC circuit can also be known as a resonant circuit, tank circuit, or tuned circuit. LC circuits can be used to pick out or generate a signal at a certain frequency. The LC circuit herein can comprise large capacitance varactors/large impedance varactors given the frequencies involved. The varactor-based circuit can be used along with the DAC to change the value of the capacitance (C), such that the LC can be tuned to different frequencies, depending on the frequency channel allocated to the FSD at a given instant. Each FSD can be allocated multiple operating frequencies at different instants. Tuning the FSDs can ensure that each FSD (e.g., each FSD out of three FSDs, etc.) can have a discrete frequency for modulation/demodulation, which can avoid cross talk between FSDs of the FMS. In various embodiments, a clock generation circuitry can be used to generate a doppler shifted frequency and driving the square wave after attenuating the square wave into the receive circuitry (e.g., the LC tank can only allow the first harmonic sine wave to pass through) can assist to automate the LC tank calibration process by changing the DAC voltage to maximize the amplitude of the shifted sine wave seen at the input of the analog-to-digital converter (ADC). In various embodiments, a pulse or signal transmitted by an FSD in an FMS can be phase shifted until the artefacts of the FSD can be brought down to zero. In this embodiment, an FSD with the highest amount of crosstalk components can act as the main FSD and other FSDs in an FMS can phase shift the respective starts of their respective transmit pulses with respect to the main FSD, until the crosstalk artefacts of the other FSDs can be reduced to zero. The phase shifting can be performed until there are no crosstalk components remaining in any of the FSDs.

Various embodiments herein can ensure that each FSD of a plurality of FSDs with a discrete or distinctly tuned frequency of an LC network can detect the reflected ultrasound wave at its own carrier frequency while minimizing crosstalk. Further, various embodiments herein can perform a periodic synchronization of Tx enable and Rx enable pulse patterns of multiple FSDs via periodic pings, either from a monitoring system or by a main FSD, to reduce crosstalk artefacts in the FMS. The embodiments discussed in the present disclosure can lead to reliable monitoring of multiple fetal hearts, which can generally indicate the more complex birth scenarios. For example, the methods disclosed herein can reduce false fetal movement detections and unwanted Doppler Audio Noises. A reduction of instances of false heart rates being produced and fetal heart-related confusion across FSDs can ensure correct interpretations by clinicians, and thereby ensure timely actions by the clinicians. During fetal distress, the embodiments discussed herein can reduce the chances of an FSD rendering an incorrect fetal heart rate and avoid an otherwise catastrophic scenario. The techniques disclosed in the present disclosure can use the same piezo crystals to generate different frequencies and electronic tuning to create a universal FSD that can work at multiple frequencies or FDM (with closer frequencies). The detection and elimination of crosstalk via the suppression of known harmonics can additionally enable clinicians to use FDM reliably without any false FHR pickups.

The embodiments depicted in one or more figures described herein are for illustration only, and as such, the architecture of embodiments is not limited to the systems, devices and/or components depicted therein, nor to any particular order, connection and/or coupling of systems, devices and/or components depicted therein. For example, in one or more embodiments, the non-limiting systems described herein, such as non-limiting system 100 as illustrated at FIG. 1, and/or systems thereof, can further comprise, be associated with and/or be coupled to one or more computer and/or computing-based elements described herein with reference to an operating environment, such as the operating environment 1400 illustrated at FIG. 14. For example, system 100 can be associated with, such as accessible via, a computing environment 1400 described below with reference to FIG. 14, such that aspects of processing can be distributed between system 100 and the computing environment 1400. In one or more described embodiments, computer and/or computing-based elements can be used in connection with implementing one or more of the systems, devices, components and/or computer-implemented operations shown and/or described in connection with FIG. 1 and/or with other figures described herein.

FIG. 1 illustrates a block diagram of an example, non-limiting system 100 that can enable multiple FSD coexistence in an FMS in accordance with one or more embodiments described herein.

System 100 and/or the components of system 100 can be employed to use hardware and/or software to solve problems that are highly technical in nature (e.g., related to ultrasound technologies, fetal monitoring, signal processing, etc.), that are not abstract and that cannot be performed as a set of mental acts by a human. Further, some of the processes performed may be performed by specialized computers for carrying out defined tasks related to ultrasound coexistence in an FMS. System 100 and/or components of system 100 can be employed to solve new problems that arise through advancements in technologies mentioned above and/or the like. System 100 can provide technical improvements to FMSs by generating lower noise in FSDs, improving sensitivity of FSDs, and eliminating artifacts. System 100 can provide additional improvements by providing higher depth coverage in FDM as compared to TDM.

Discussion turns briefly to processor 102, memory 104 and bus 106 of system 100. For example, in one or more embodiments, system 100 can comprise processor 102 (e.g., computer processing unit, microprocessor, classical processor, and/or like processor). In one or more embodiments, a component associated with system 100, as described herein with or without reference to the one or more figures of the one or more embodiments, can comprise one or more computer and/or machine readable, writable and/or executable components and/or instructions that can be executed by processor 102 to enable performance of one or more processes defined by such component(s) and/or instruction(s).

In one or more embodiments, system 100 can comprise a computer-readable memory (e.g., memory 104) that can be operably connected to the processor 102. Memory 104 can store computer-executable instructions that, upon execution by processor 102, can cause processor 102 and/or one or more other components of system 100 (e.g., frequency generation component 108, storage component 110, separation component 112, signal processing component 114, and/or synchronization component 116) to perform one or more actions. In one or more embodiments, memory 104 can store computer-executable components (e.g., frequency generation component 108, storage component 110, separation component 112, signal processing component 114, and/or synchronization component 116).

System 100 and/or a component thereof as described herein, can be communicatively, electrically, operatively, optically and/or otherwise coupled to one another via bus 106. Bus 106 can comprise one or more of a memory bus, memory controller, peripheral bus, external bus, local bus, and/or another type of bus that can employ one or more bus architectures. One or more of these examples of bus 106 can be employed. In one or more embodiments, system 100 can be coupled (e.g., communicatively, electrically, operatively, optically and/or like function) to one or more external systems (e.g., a non-illustrated electrical output production system, one or more output targets, an output target controller and/or the like), sources and/or devices (e.g., classical computing devices, communication devices and/or like devices), such as via a network. In one or more embodiments, one or more of the components of system 100 can reside in the cloud, and/or can reside locally in a local computing environment (e.g., at a specified location(s)).

In addition to the processor 102 and/or memory 104 described above, system 100 can comprise one or more computer and/or machine readable, writable and/or executable components and/or instructions that, when executed by processor 102, can enable performance of one or more operations defined by such component(s) and/or instruction(s). For example, in various embodiments, frequency generation component 108 can use a variable frequency generator circuitry (or variable frequency generation block) to generate electronic signals at one or more different frequencies (e.g., frequencies 118) in at least one FSD of an FMS, wherein the at least one FSD can dynamically adjust a transmit voltage of the at least one FSD to maintain one acoustic power value (i.e., the same acoustic power value) at the one or more different frequencies, wherein the electronic signals can cause a transducer of the at least one FSD to generate ultrasound signals at the one or more different frequencies. For example, various embodiments herein can implement FDM to monitor multiple fetuses simultaneously, wherein each sensor (i.e., each FSD) in an FMS can be configured by frequency generation component 108 to operate at different frequencies, using the variable frequency generator circuitry. Further, each sensor of the FMS can be completely reconfigurable, which can simplify the task of fetal monitoring for a clinician or a caregiver. For example, an FMS can comprise three sensors, sensor A, sensor B and sensor C, wherein each of sensor A, sensor B and sensor C can operate at any of three frequencies, F1, F2 and F3, depending on an order of connection of sensors A, B and C. For example, in one scenario, sensor A can be connected first followed by sensor B and sensor C to generate frequencies F1, F2 and F3. In a different scenario, sensor C can be connected first followed by sensor B and sensor A to generate frequencies F3, F2 and F1. For example, in a monitoring session, a sensor (e.g., sensor A, sensor B or sensor C) can correspond to a frequency that the sensor is latched on to. If the monitoring session ends and a new monitoring session begins, the first cable (associated with a sensor) that can become connected can take the frequency F1. However, in a monitoring session with sensors A, B and C, if the sensors are disconnected and reconnected, the sensors can revert to generate frequencies F1, F2 and F3, respectively. The embodiments discussed herein can ensure good performance and efficiency of the FMS at all three frequencies using the same transducer. The FMS can also be configurable in terms of the number of FSDs, for example, to include two FSDs for monitoring twin fetuses, three FSDs for monitoring triple fetuses, and so on. Thus, each fetus can be monitored with a dedicated FSD that can send pulses (ultrasound signals) and receive pulses reflected from the fetus. It is to be appreciated that, a transducer refers to a piezoelectric element (that is, the transducer is a piezo crystal) that can convert electrical energy into mechanical energy, and the transducer can be a passive portion of an FSD/sensor.

Further, various embodiments herein can ensure that a transducer of an FSD receives only the signals having a frequency equal to the frequency of operation/carrier frequency of the transducer, to prevent signals from other FSDs having different carrier frequencies from being detected by the transducer. In other words, various embodiments herein can isolate the FSD to prevent the FSD from detecting a heartbeat or fetal movement of a fetus not being monitored by the FSD, and thereby prevent confusing the FSD. As such, various embodiments herein can enable a transducer to receive pulses at different frequencies, based on a carrier frequency of the FSD. For example, in various embodiments, the FSD can comprise a tunable LC tank circuit comprising large capacitance varactors that can tune a resonant frequency of the tunable LC tank circuit to a carrier frequency of the at least one FSD, wherein tuning the resonant frequency of the tunable LC tank circuit to the carrier frequency of the at least one FSD can comprise using a DAC to adjust biasing voltages of a balanced varactor network to dynamically change a capacitance value of the large capacitance varactors, and wherein the carrier frequency is a frequency selected from the one or more different frequencies generated by frequency generation component 108, which is described in greater detail infra. In some embodiments, tuning the resonant frequency of the tunable LC tank circuit to the carrier frequency of the at least one FSD can comprise using a voltage control mechanism other than a DAC, wherein the voltage control mechanism can be a resistor divider network, a DC regulator (that can generate a DC regulated voltage), or another type of voltage control mechanism. The tunable LC tank circuit can be a narrow band transducer, and the tunable LC tank can substantially reject (i.e., reject to a large extent) frequencies different than the carrier frequency of the FSD due to the resonant frequency of the tunable LC tank circuit being tuned to the carrier frequency of the FSD. The tunable LC tank circuit can provide narrowband amplification around a frequency of interest, thereby offering attenuation/partial rejection of small signals of other frequencies. In various embodiments, the tunable LC tank circuit can also act as an impedance matching circuitry to minimize a phase difference between current and voltage from the transducer to the receiver circuitry (by eliminating the imaginary components of impedance).

Further, the tunable LC tank circuit can assist to generate a high gain and a low noise amplification. For example, tuning the resonant frequency of the tunable LC tank circuit to the carrier frequency of the FSD can improve reception sensitivity and gain of the tunable LC tank circuit at the carrier frequency. Tuning the resonant frequency of the tunable LC tank circuit to the carrier frequency of the FSD can also desensitize the FSD to respective carrier frequencies of additional FSDs. Additionally, tuning the resonant frequency of the tunable LC tank circuit to the carrier frequency of the FSD can characterize and compensates for a behavior of the resonant frequency of the tunable LC tank circuit resulting from temperature fluctuations experienced by the FSD to cause the tunable LC tank circuit to exhibit a consistent performance despite the temperature fluctuations. For example, the resonant frequency of the tunable LC tank circuit can be tuned once, but temperature fluctuations can shift the tuning frequency by offsetting the tuning frequency. Various embodiments herein can characterize the temperature characteristics and keep altering the tuning frequency value in real time to maintain performance of the tunable LC tank circuit. For example, in various embodiments, as the operating temperature of an FSD changes, the DAC value can also be changed to compensate for the LC tank's thermal characteristics. In various embodiments, the variable frequency generator circuitry can use an attenuated shifted frequency to automate a calibration process for the tunable LC tank circuit. In some embodiments, the attenuated shifted frequency can be a doppler shifted frequency. In other embodiments, the carrier wave can be offset with a smaller value representative of what can be seen in a doppler shift resulting from fetal heart tissue movement. In regard to the above discussion, the variable frequency generator circuitry and the tunable LC tank circuit are described in greater detail infra, and with reference to FIGS. 3, 4 and 5.

Clock Generator:

The variable frequency generator circuitry can be a clock generator (i.e., a tunable clock generator) that can generate odd frequencies (e.g., 1.151 megahertz (MHz), 1.162 MHz, etc.) and the clock generator can be programmed to generate frequencies based on a frequency allotted to the clock generator by a monitor or a main device. The clock generator can generate frequencies with high accuracy (e.g., down to 1 part per million (ppm)) as well as very low jitters (e.g., 100-200 picoseconds (ps) or lower). The clock generator can assist with generating pulses to be transmitted, receiving pulses, and switching needed for actuation and pulsing in conjunction with digital logic implemented ahead of the clock generator, to generate variable clocks. In various embodiments, each FSD of the FMS can comprise a clock generator and the clock generator can be used (e.g., by frequency generation component 108) to generate modulation (MOD) frequencies for exciting a piezo crystal, wherein a MOD frequency can refer to a carrier frequency such as, for example, 1.151 MHz, 1.162 MHz, etc., of an FSD. It is to be appreciated that the terms MOD frequency and carrier frequency have been used interchangeably throughout this specification. For example, the clock generator can excite a piezo crystal (i.e., transducer) for generating ultrasound waves that can be directed at a fetus, reflect off the fetus and return to the piezo crystal. For exciting the piezo crystal, the clock generator can generate a clock signal, wherein the clock signal is an electronic signal that can oscillate at a specific MOD frequency. The clock generator can provide a base frequency based on which a wave can be shaped and driven by a dedicated circuitry inside the FSD to drive the piezo crystal. Thereafter, the piezo crystal can convert the received reflected ultrasound wave into electrical energy that can be processed during a signal processing stage. The clock generator can comprise a quartz crystal, such as those commonly used in electronic devices. It is to be appreciated that the quartz crystal and the piezo crystal are different elements. As noted supra, the piezo crystal can be used to transmit and receive ultrasound waves but not for generating a clock used for generating different frequencies, as discussed herein. The clock generator can further comprise a fractional multiplier that can be a phase locked loop (PLL) for multiplying a crystal frequency by a value, X, and further dividing the result to generate a desired MOD frequency (e.g., frequencies 118). For example, the clock generator can generate a MOD frequency, a second frequency equal to 8×MOD frequency and a third frequency equal to MOD frequency+200 hertz (Hz). The MOD frequency can be used to drive and actuate the piezo crystal in the FSD. The 8×MOD frequency can be a higher frequency generated by the clock generator and needed for driving a processor, and the 8×MOD frequency can be sent to the processor to drive the digital logic inside the processor. The MOD frequency+ 200 Hz frequency can be used for calibrating the tunable LC tank circuitry. It is to be appreciated that the frequencies described herein are exemplary and not specific. Thus, the clock generator can be employed (e.g., by frequency generation component 108) to generate multiple MOD frequencies.

Tunable LC Tank Circuit:

The signal reflected by a fetus (i.e., reflected signal) to the piezo crystal in the FSD can be directly processed by the LC tank circuit. For example, an input to the tunable LC tank circuit can be an electrical signal received from the piezo crystal and generated by the piezo crystal by converting ultrasonic waves reflected by a fetus into electrical energy. The tunable LC tank circuit can comprise an inductor and a capacitor, wherein the inductor can be a simple inductor and the capacitor can be a simple capacitor. It is known that an inductor and capacitor together can form a resonant circuit. As discussed above, the tunable LC tank circuit can further comprise large capacitance varactors that can tune a resonant frequency of the tunable LC tank circuit to a carrier frequency of the FSD. Varactors are elements like diodes. However, varactors can have a tunable capacitance, wherein based on a biasing voltage, the capacitance of a varactor can be tuned. The capacitor of the tunable LC tank circuit can be split into multiple sections for fine-tuning the exact capacitance value. For example, the capacitance of the tunable LC tank circuit can be split into two parallel capacitances from two capacitors connected in parallel, followed by capacitance from the varactors and some additional capacitance from diodes in the tunable LC tank circuit. The capacitance values from the two parallel capacitors and the diodes can be fixed values, and the varactors can generate variable capacitance. Varactors can be introduced in the tunable LC tank circuit to precisely tune an FSD by tuning the varactors to generate a precise capacitance representative of the carrier frequency of the FSD. For example, when FSDs are manufactured, the respective capacitances on board the FSDs can vary from unit to unit due to presence of dust, amount of solder, etc. Due to manufacturing process variations, parasitic capacitances and inductance can also offset the turning for fixed capacitances. Therefore, tuning the resonant frequency of the tunable LC tank circuit on each device (e.g., each FSD) can be beneficial. A frequency of resonance/resonant frequency (f) of an FSD can be determined using Equation 1.

$$f = \frac{1}{2\pi\sqrt{LC}}$$ <span style="float:right">Equation 1</span>

It is evident from Equation 1, that the capacitance value of the tunable LC tank circuit can determine the frequency that the tunable LC tank circuit can be tuned to. In this regard, tuning the tunable LC tank circuit to the carrier frequency can result in better gain and sensitivity at the carrier frequency, as discussed in various embodiments herein. During operation, a reflected ultrasound signal received by the piezo crystal and converted to electrical energy can enter the three capacitors including the two capacitors connected in parallel and the diodes of the tunable LC tank circuit. Once the electrical signal is tuned, the electrical signal can oscillate back and forth between the inductor-capacitor and the mid-point of the tunable LC tank circuit, and the electrical signal can become amplified. Thereafter, the amplified signal can proceed to subsequent amplification sections. In this manner, the tunable LC tank circuit can pre amplify the electrical signal.

Various embodiments herein can also address a variety of crosstalk scenarios that can be generated in the FMS. Usually, in case of multiple FSDs, an FMS can be designed for microvolt (μV) and sub-microvolt (sub-μV) level signals because an FSD can expect to receive only a small portion of a signal in the form of a reflected signal. However, in a scenario with two FSDs placed directly across from one another and directing ultrasound pulses into each other, the FSDs can be expected to receive higher volt (V) level signals. In such a scenario, the ultrasound pulses received by an FSD can also include strong reflected signals corresponding to signals transmitted by the other FSD based on the two FSDs feeding signals into each other. Such scenarios can generate crosstalk, wherein the tunable LC tank circuit of an FSD cannot completely attenuate and prevent the unwanted signals from other FSDs from entering the FSD. That is because the respective amplitudes of the signals from transducers of other FSDs can be very large, and signal attenuation cannot assist with the cause. Several problems can arise due to crosstalk, causing a false heartbeat to be generated, which can be a serious problem in fetal monitoring.

In this regard, system 100 can generate predictable outcomes from all crosstalk scenarios to selectively eliminate all artifacts. For example, in various embodiments, separation component 112 can separate respective carrier frequencies of the plurality of FSDs in the FMS such that a frequency difference between carrier frequencies of any two FSDs is not a multiple of a PRR of either FSD. Stated differently, separation component 112 can separate a MOD frequency of an FSD in the FMS such that a difference of MOD frequencies of the FSD and another FSD cannot be a multiple of a PRR of the other FSD. The MOD frequency of an FSD being the internal higher carrier frequency transmitted by the FSD, the difference of MOD frequencies of two FSDs cannot be a multiple of the PRR of either FSD because such a scenario can cause aliasing and signal confusion. As such, isolating the MOD frequencies can prevent interference between the two FSDs. The PRR of an FSD can be defined as one complete cycle of transmitting a signal and receiving a reflected signal. In other words, the PRR of an FSD can be defined as the rate at which one complete cycle, consisting of periods of transmission Tx and reception Rx of pulses can occur for the FSD. Differently, the PRR refers to the number of ultrasound pulses emitted per a defined time period, or more particularly, as the rate of repetition of the Tx and Rx periods. For example, an FSD can transmit ultrasound pulses at a carrier frequency over a duration of transmit (Tx) and receive corresponding reflected pulses every 250 microseconds (μs) causing the PRR of the FSD to be 4 kilohertz (kHz), according to Equation 1. In various embodiments, separation component 112 can select odd frequencies (e.g., 1.152 MHz 1.162 MHz, etc.) as carrier frequencies of FSDs in the FMS, such that the difference of any two MOD frequencies is not a multiple of the PRR of an FSD, to generate predictable harmonics that can be used to control crosstalk. Equation 2 can be used (e.g., by separation component 112) to determine a difference (delta/Δ) between MOD frequencies of transducers for separating the MOD frequency of one transducer based on that of another. That is, the MOD frequencies of two transducers can be separated by using Equation 2.

$(p \times (p-1)-1)$ kHz, wherein '$p$' represents the PRR of
the FSD in kHz. <span style="float:right">Equation 2:</span>

Separating MOD frequencies using the method described above can make crosstalk predictable and easier to eliminate, wherein crosstalk can otherwise remain unrealized as crosstalk. For example, separating the MOD frequencies/respective carrier frequencies of transducers can generate predictable harmonics during crosstalk in the FMS, wherein the predictable harmonics can be selectively eliminated during a signal processing stage of a sensor. For example, separating the respective carrier frequencies of (a plurality) of FSDs can cause a first carrier frequency of a first FSD of the plurality of FSDs to become demodulated by a second carrier frequency of a second FSD of the plurality of FSDs, which can generate predictable harmonics in the FMS. For example, for p=4 in Equation 2, every 1 kHz from 1 kHz to (p−1) kHz can generate harmonics of 1 kHz, 2 kHz and 3 kHz that can be eliminated to avoid crosstalk. Normally, fetal monitoring can involve sub-kHz level frequencies as opposed to specific frequencies (e.g., 1 kHz, 2 kHz, 3 kHz, etc.), and clinicians can look for a fetal heart rate and variability in heart rate during fetal monitoring. The harmonics and effects of the corresponding crosstalk can be eliminated by implementing a filter that can notch the harmonic frequencies and by implementing an AGC stage that can normalize signal amplitudes. For example, in various embodiments, signal processing component 114 can implement an AGC stage and a filter to selectively eliminate the predictable harmonics to eliminate crosstalk in the FMS, wherein the automatic gain control stage can be implemented as a software, a hardware or a combination of the software and the hardware. Normalizing the signal amplitudes can remove extremely low frequencies created due to crosstalk, and a notch filter can be implemented every 1 kHz, wherein the notch filter can the clean the harmonics. As previously stated, the AGC stage can be implemented as a firmware/signal processing software algorithm and the filter can be implemented after the AGC stage to eliminate the 1 kHz, 2 kHz and 3 kHz harmonics that can interfere with fetal heart rate detection. The 1 kHz filter and the algorithm for the AGC stage can both be implemented in a signal processing core in the microcontroller. The AGC stage and the 1 kHz filter can be implemented much later than the tunable LC tank circuitry in the signal chain. In an embodiment, the filter can be implemented without implementing the AGC stage; however, a performance trade-off can be expected without the AGC stage.

Eliminating crosstalk by separating MOD frequencies of transducers and generating predictable harmonics can rely on accuracy of a MOD frequency generated by the clock generator. For example, the method discussed above can need highly accurate frequencies for generating predictable harmonics because inaccuracies in MOD frequencies can generate significant noise in addition to harmonics. For example, inaccuracies in MOD frequencies can generate differences between frequencies, wherein such differences are not a multiple of the 1 kHz, 2 kHz or 3 kHz harmonics. To ensure that accurate MOD frequencies are generated by the clock generator of an FSD, a frequency calibration technique can be implemented during manufacturing of an FSD. The frequency calibration technique can compensate for the inaccuracies of MOD frequencies by generating frequencies that can be offset based on an input clock. For example, if a clock generator generates a MOD frequency of 1.151 MHz+5 Hz, the clock generator can be reconfigured (e.g., by frequency generation component 108) to generate 1.151 MHz−5 Hz, such that the overall frequency generated by the clock generator can be 1.151 MHz. The design of the FSD can include a provision to calibrate the MOD frequencies generated by the FSD up to an accuracy of about 1 Hz or lower. Calibration of the FSD can be performed by measuring the frequency generated by the clock generator in real-time and compensating for the frequency generated by the clock generator. The calibration can be a digital calibration performed (e.g., by frequency generation component 108) via a software.

In various embodiments, synchronization component 116 can perform a periodic PRR synchronization to synchronize a start of a transmit period of the FSD with respective starts of transmit periods of one or more additional FSDs in the FMS to prevent the ultrasound signals generated by the FSD from becoming demodulated by respective carrier frequencies generated by the one or more additional FSDs in the FMS, to prevent crosstalk in the FMS. It is to be appreciated that ultrasound signals generated by an FSD can be demodulated by another FSD after the ultrasound signals from the FSD being received by the other FSD, converted to electrical signals by the transducer (piezo crystal) of the other FSD, and processed by the tunable LC tank circuitry of the other FSD. Synchronization component 116 can synchronize the beginning of a transmit period of an FSD with respect to another FSD and synchronize respective PRRs of FSDs in the FMS such that the respective PRRs can remain synchronized even in case of a minor offset in MOD frequencies generated by respective clock generators of the transducers. For example, due to clock differences between transducers, one transducer can have a PRR of 3.9 kHz whereas another transducer can have a PRR of 4 kHz. In this case, synchronization component 116 can perform a periodic PRR synchronization to ensure that both transducers can transmit pulses at a PRR of 4 kHz. A PRR synchronization can involve synchronization of the start of a transmit (Tx) pulse of an FSD with the start of a Tx pulse of another FSD. It should be noted that the PRR of 3.9 kHz does not become fixed at 4 kHz after the synchronization, that is, the PRR synchronization can prevent the respective transmit pulses (Txs) and receive pulses (Rxs) of FSDs from drifting across each other substantially to prevent creation of any crosstalk via low frequency harmonics without changing the PRR of an FSD. As such, the PRR synchronization can prevent the generation of lower frequency noise during crosstalk. Generally, the difference in PRRs can be in single digit frequencies (Hz) or much lower (e.g., in millihertz (mHz)). Long before the Tx pulse of an FSD can overlap an entire pulse repetition period, synchronization component 116 can synchronize (periodically, only once in a while) the beginning of the transmit period of the FSD with respect to another FSD or a central hub to bring the start of the transmit period back to the original position and cut back on the drift. The frequency of performing the synchronization can be dictated by the maximum possible frequency offsets between any two sensors, and the frequency can be much higher than a frequency difference offset from an ideal expected difference. For example, a 10 mHz difference in PRRs of any two FSDs can imply that a synchronization can be performed every 100 mHz such that before a 10% drift, the Tx pulse can be brought back to the original position. That is, the synchronization can be performed every 10 seconds. PRR synchronization can ensure that respective Tx pulses of FSDs can pulse at the same time.

As stated above, the periodic PRR synchronization can be performed by using a monitor to generate a ping in real time or by using electrodes and a main transducer to transmit signals to the additional transducers. In some embodiments, the signals transmitted by the main transducer can be high-frequency low-current signals. The periodic PRR synchronization can be performed wirelessly or through wired connections, that is, the synchronization can also be performed in wired FSD systems. For example, synchronization component 116 can synchronize the beginnings of the transmit periods of FSDs either via a main hub or monitor that can act as a main device for controlling the transducers of the FMS, or via an FSD that can control other transducers in the FMS. In some embodiments, the PRR synchronization can be implemented without implementing the AGC stage (i.e., by using only the filters) after separating the respective MOD frequencies of the transducers to generate the predictable harmonics. In other embodiments, the PRR synchronization technique can be implemented alongside the AGC stage with filters for eliminating the crosstalk.

Synchronizing the PRRs of FSDs can remove lower frequency noises generated in the FMS, but not the harmonics (e.g., 1 kHz, 2 kHz, etc.). Further, since ultrasound can travel relatively slowly, PRR synchronization may not be helpful in some scenarios. In a fetal monitoring scenario where two FSDs can be positioned directly across from each other on the abdomen of a pregnant woman, a signal transmitted from a first FSD of the two FSDs can enter the reception period of the second FSD. The reception period of an FSD can refer to the period after an FSD has transmitted a signal during which time the FSD can expect to receive a reflected signal. Thus, the second FSD can receive the signal transmitted by the first FSD as well as a reflected signal corresponding to the signal transmitted by the second FSD. The strength of the signal transmitted by the first FSD and received by the second FSD can be high due to the signal from the first FSD being direct, and such a scenario can generate 1 kHz, 2 kHz, 3 kHz, etc. harmonics. At the same time, the first FSD can also receive the signal transmitted by the second FSD and a reflected signal corresponding to the signal transmitted by the first FSD.

In this regard, various embodiments herein can enable additional techniques to prevent crosstalk in the scenario discussed herein. For example, in various embodiments, synchronization component 116 can perform a pulse phase synchronization using a control system to prevent a signal transmitted by a first FSD from entering a receive period of a second FSD located directly across the first FSD at a distance, wherein the control system can measure an amount of harmonics generated by the first FSD at the second FSD and gradually shift a phase of the signal transmitted by the first FSD to align the signal transmitted by the first FSD with a signal transmitted by the second FSD in the FMS. For example, the first FSD can be operatively coupled to a control system without coupling the second FSD to the control system. The control system can measure an amount of harmonics (e.g., using synchronization component 116) being generated by the first FSD at the second FSD (because the second FSD can be demodulating transmit pulses/signals of first FSD), and the control system can gradually phase shift a signal transmitted by the first FSD, which can cause the signal transmitted by the first FSD to overlap the signal transmitted by the second FSD and prevent the signal transmitted by the first FSD from entering the reception period of the second FSD.

Thus, synchronization component 116 can shift the phase of a signal from one FSD to align the signal with another signal from another FSD to prevent the signal from entering the receive period of the other FSD. This can be done by accounting for the travel times of the signals from the FSDs. Such a technique can eliminate the need to remove crosstalk. Additionally, during crosstalk, a reflected signal (e.g., signals reflected from a fetus) received by an FSD can sometimes be very weak, and in this case, a direct signal received by the FSD from another FSD, in addition to the reflected signal, can saturate the reflected signal. In this scenario, the reflected signal can become lost even if crosstalk is eliminated. Phase shifting signals as described above, can prevent saturation of the reflected signal and improve reception sensitivity of FSDs. That is, aligning the respective signals transmitted by the FSDs can prevent any large signals from flooding the respective receive chains of either FSD during their respective reception periods. This can allow a larger amount of voltage to be available for an FSD to receive a reflected signal and amplify the reflected signal, for example, as compared to the scenario wherein a transducer can be receiving the reflected signal and a transmitted signal from another transducer.

More specifically, using the predictable harmonics (1 kHz, 2 kHz, etc.), the control system can move a transmitted signal/pulse (Tx) in time (i.e., change the phase of the pulse). In this embodiment, the PRR of the transmitted pulse can remain unchanged, and the control system can shift the Tx pulse from an FSD to the right or left in time and monitor the harmonics being generated to determine when the harmonics disappear. The Tx pulses from two FSDs can continue to transmit regularly with a constant time difference (e.g., 50 microseconds (μs), 60 μs, etc.). That is, the PRRs of the Tx pulses can remain the same, but the position of a Tx pulse can be different in time as a result of the phase shifting. Thus, by the time a Tx pulse from one FSD can reach a second FSD, the Tx pulse can blast into the second FSD's transmit instead of encroaching upon the receive period of the second FSD. As such, phase shifting can prevent a crosstalk pulse from being received by an FSD and crosstalk can be negated.

In various embodiments, by synchronizing the phases and the PRRs of respective transmits pulses of FSDs in an FMS, the implementation of the AGC stage with filters can be avoided.

Figure 2:
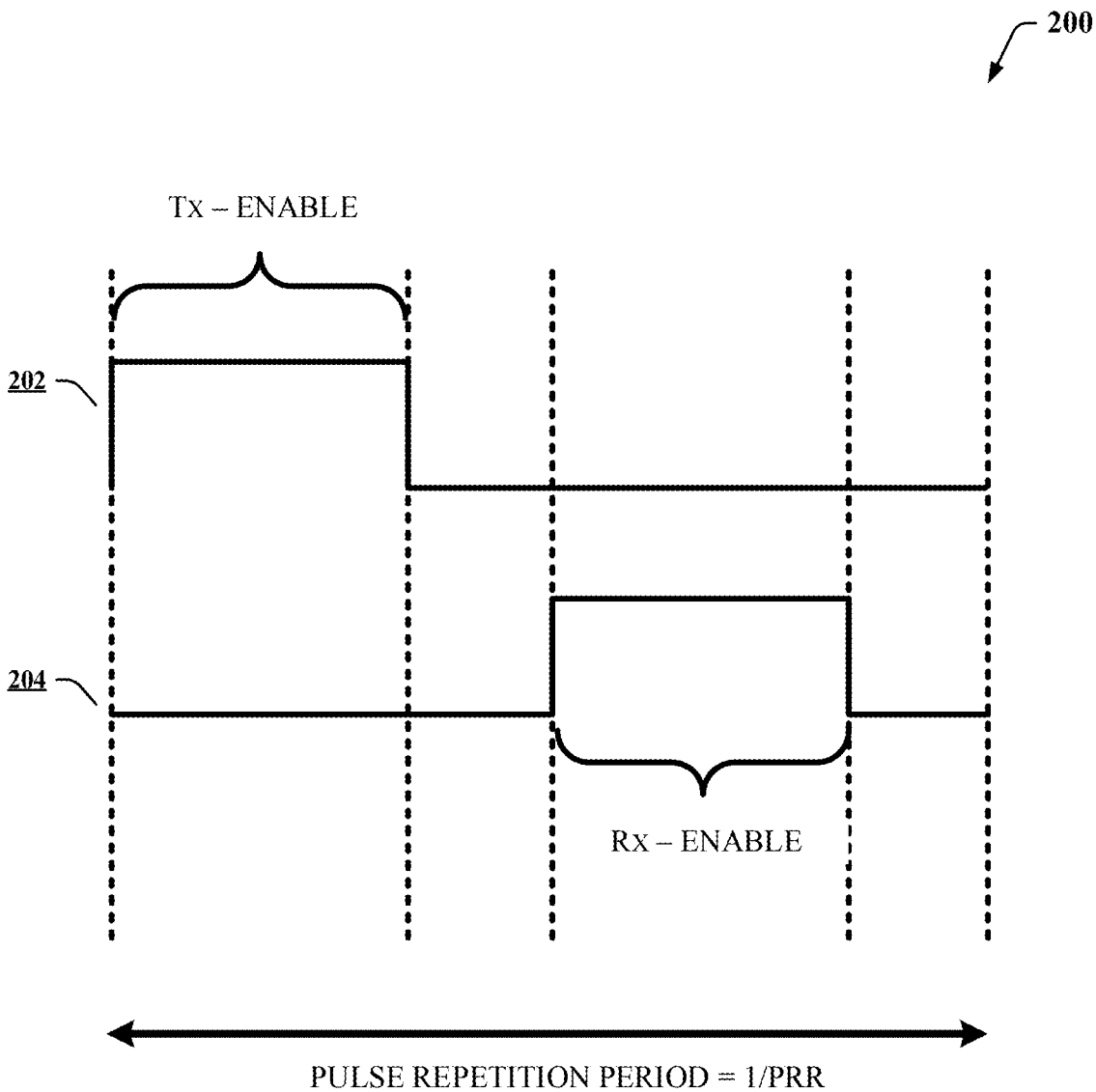
FIG. 2 illustrates a diagram of an example, non-limiting pulse repetition period in accordance with one or more embodiments described herein.

FIG. 2 illustrates a diagram of an example, non-limiting pulse repetition period 200 in accordance with one or more embodiments described herein. One or more embodiments described with reference to FIG. 2 can be enabled by one or more components of system 100. Repetitive description of like elements and/or processes employed in respective embodiments is omitted for sake of brevity.

Generally, FSDs use a lower acoustic power as compared to ultrasound imaging that can use higher acoustic powers, which can allow fetal monitoring for longer durations. Transducers work on the principle of doppler shift, wherein a pulse can be transmitted from a sensor at an object or location of interest and the sensor can look for a reflected signal. In case of fetal monitoring, a reflected signal having a doppler shifted frequency can indicate that a movement has been detected. Clinicians can use FSDs to detect regular movements that can be correlated to fetal heartbeats and used to determine the heartrate of a fetus. FSDs can also be used to detect lower frequency movements such as movements related to breathing, rotational or other movement of the fetus inside a mother's womb, etc., and different frequencies can be used to identify fetal movements and fetal heartrates. Typically, sensors can operate in TDM or FDM. Most sensors operate under TDM, wherein one sensor in a system of sensors can transmit a pulse and receive a reflected pulse followed by another sensor transmitting and receiving pulses, as opposed to all sensors in the system of sensors transmitting and receiving pulses at once or in a non-related random sequence. Thus, in TDM, each sensor can complete one cycle of transmitting and receiving pluses in succession, and the TDM cycle can continue to alternate between sensors. TDM can prevent interferences between transducers and sensors. However, monitoring multiple fetuses (e.g., for triplets, quadruplets, etc.) can be challenging with TDM due to less sensing time availability. Further, a signal quality can be compromised under TDM. In this regard, various embodiments discussed herein can allow multiple sensors to work simultaneously using FDM.

In accordance with various embodiments discussed herein, non-limiting pulse repetition period 200 (pulse repetition period 200) can represent a period during which an FSD can transmit a signal, as illustrated by transmit signal 202, and receive a reflected signal corresponding to transmit signal 202, as illustrated by receive signal 204. The pulse repetition period of the FSD can be related to the PRR of the FSD according to Equation 3.

$$\text{Pulse repetition period} = \frac{1}{PRR} \qquad \text{Equation 3}$$

It is known that for FDM in an ultrasound doppler system, piezoelectric crystals with different center frequencies need to be used. However, as seen in the FEM simulations presented in FIG. 5, the range of frequencies at which maximum sensitivity can be achieved is large enough to accommodate multiple carrier frequencies that can be separated to be reasonably far apart from one another. In this regard, various embodiments of the present disclosure can make a transducer operate at multiple frequencies and ensure consistent performance of the transducer at every frequency. Doing so can enable an FMS to operate with universal FSDs that can reconfigure themselves and be used interchangeably. The separation of frequencies using the same crystals may not be sufficient to completely avoid crosstalk unless the carrier frequencies can be chosen appropriately along with additional artifact elimination techniques. As such, methods to achieve multiple frequencies with a single transducer and selection of carrier frequencies with artifact elimination techniques are disclosed with reference to the subsequent figures.

Figure 3:
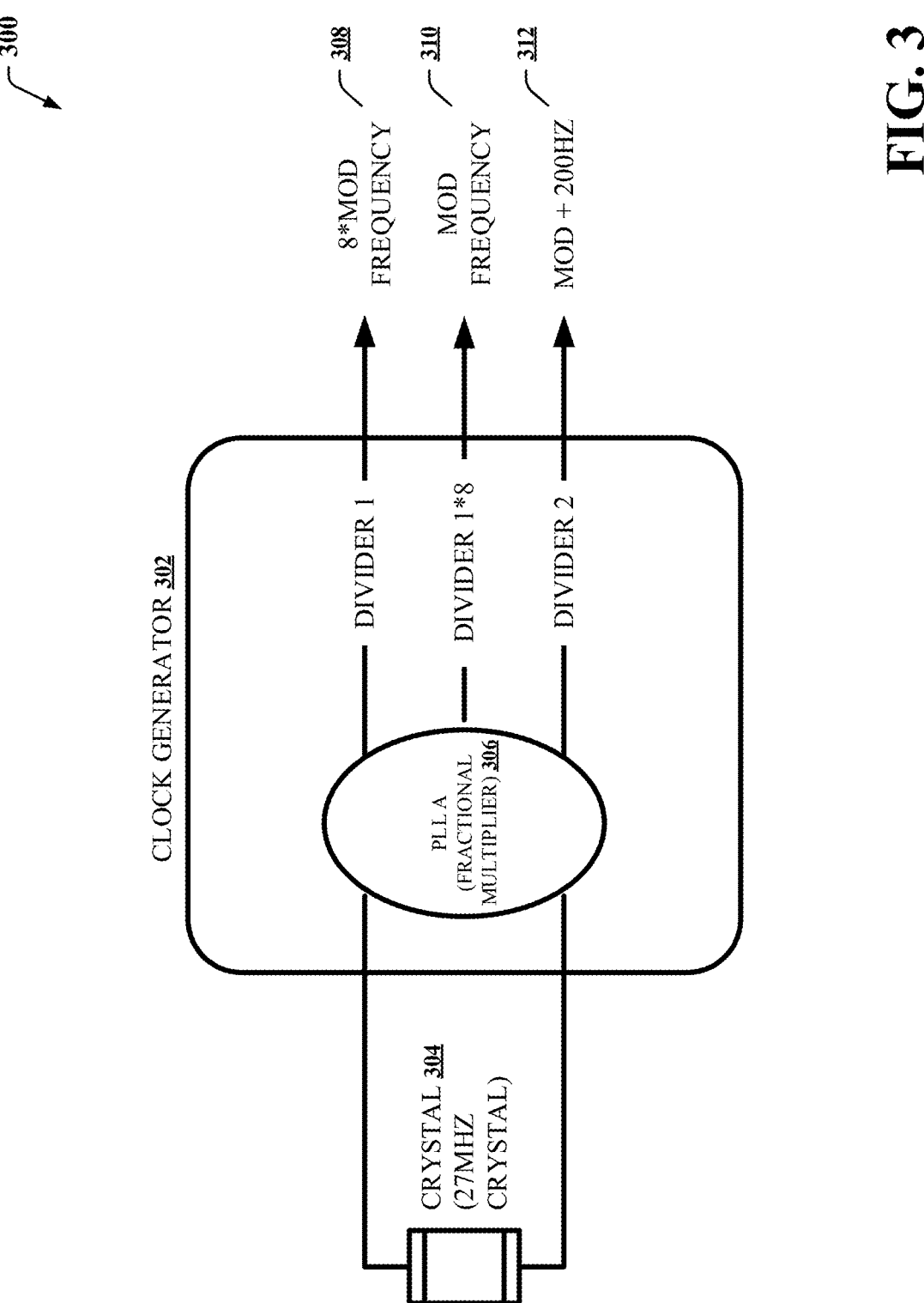
FIG. 3 illustrates a block diagram of an example, non-limiting clock generator that can generate one or more different frequencies in an FSD in accordance with one or more embodiments described herein.

FIG. 3 illustrates a block diagram 300 of an example, non-limiting clock generator that can generate one or more different frequencies in an FSD in accordance with one or more embodiments described herein. One or more embodiments described with reference to FIG. 3 can be enabled by one or more components of system 100. Repetitive description of like elements and/or processes employed in respective embodiments is omitted for sake of brevity.

Figure 4:
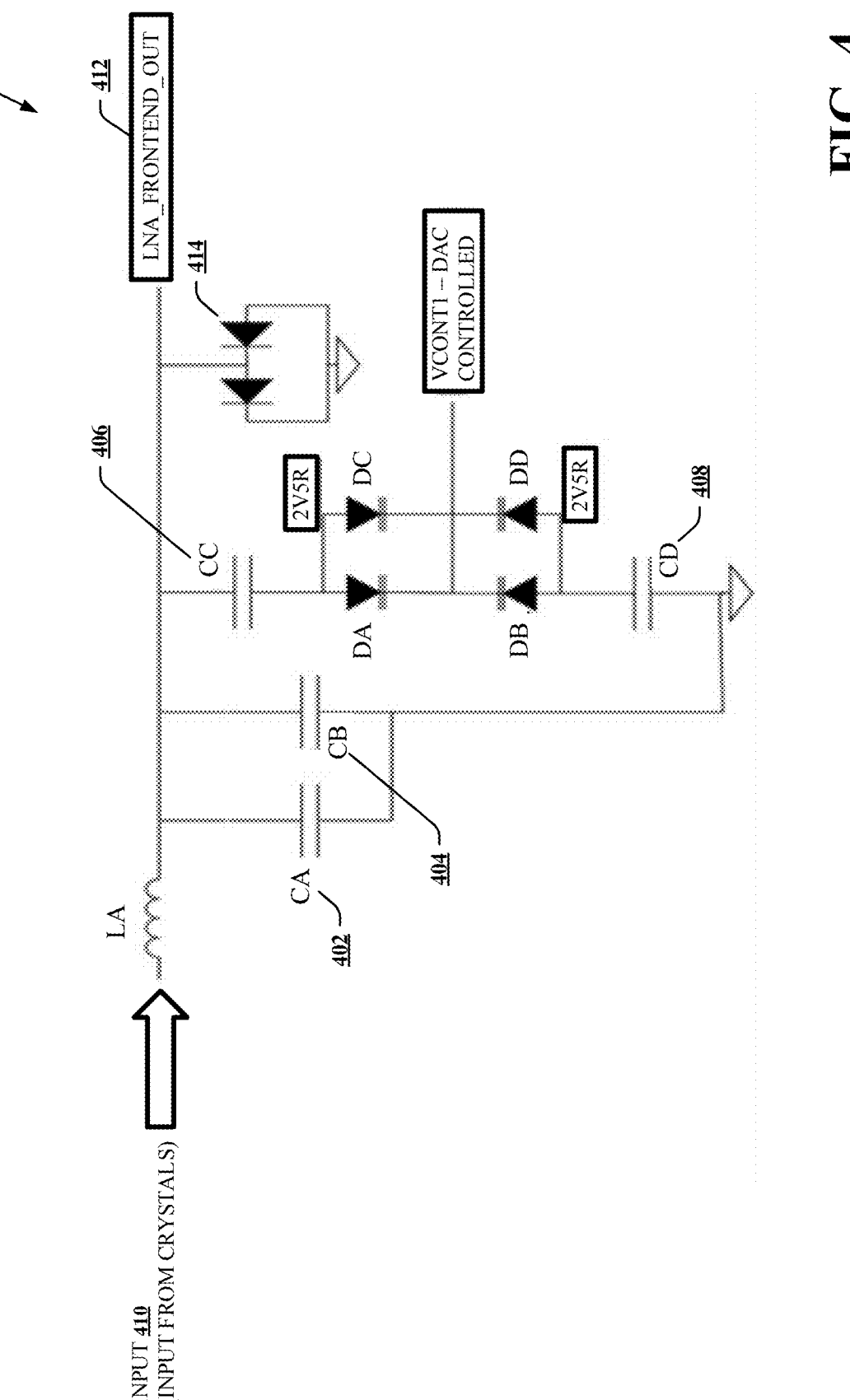
FIG. 4 illustrates a circuit diagram of an example, non-limiting tunable LC tank circuit comprising large capacitance varactors in accordance with one or more embodiments described herein.

As discussed with reference to FIG. 1, frequency generation component 108 can use a variable frequency generator circuitry (or variable frequency generation block) to generate multiple different desired frequencies in an FSD of an FMS, wherein the FSD can dynamically adjust a transmit voltage of the FSD to maintain the same acoustic power value at the one or more different frequencies. The range of frequencies at which maximum sensitivity can be achieved for an FSD can be large enough to accommodate multiple carrier frequencies that can be separated to be reasonably far apart from one another. As such, embodiments disclosed herein for artifact elimination can ensure that the multiple carrier frequencies can be sufficiently far enough (e.g., despite being close by) to separate the signals. Coupled with the crosstalk elimination techniques discussed in one or more embodiments, the range of frequencies can be sufficient to handle any artifacts. For reception sensitivity, the FSD can utilize the tunable LC tank circuit having large capacitance varactors as illustrated in FIG. 4. Using a DAC (or other voltage control mechanism), the biasing voltages of a balanced varactor network can be adjusted to tune the resonant frequency of the LC tank to a corresponding FDM frequency (i.e., a carrier frequency of the FSD). It is to be appreciated that the terms 'tunable LC tank circuit,' 'tunable LC tank circuitry,' 'LC tank' and 'LC circuit' are used interchangeably throughout this specification. An LC circuit (also known as an LC filter or LC network) can be defined as an electrical circuit consisting of passive circuit elements including an inductor and a capacitor connected together. The LC circuit can also be known as a resonant circuit, tank circuit, or tuned circuit. LC circuits can be used to selectively pick out or generate a signal at a certain frequency.

The purpose of the LC tank can be three-fold. For example, the LC tank can provide noiseless amplification of the receive signal, act as a filter and only offer narrowband amplification of each specific frequency, thereby providing some isolation from other FDM frequencies in a multi transducer system (e.g., the FMS), and optimize the loop gain of the system. The open loop gain can be directly proportional to a conversion efficiency of a transducer and the cosine of the phase difference between current and voltage from the transducer to the receiver circuitry. The LC network can act as an impedance matching circuitry to minimize the phase difference, thereby maximizing the cosine value to improve open loop gain.

In various embodiments, the variable frequency generator circuitry can generate an attenuated shifted frequency (that simulates a doppler shifted reflected signal) to automate a calibration process for the tunable LC tank circuit. The variable frequency generator circuitry can be a clock generator (e.g., clock generator 302) that can generate odd frequencies (e.g., 1.151 MHz, 1.162 MHz, etc.) and clock generator 302 can be programmed to generate frequencies based on a frequency allotted to clock generator 302 by a monitor or a main device. The clock generator can assist with generating pulses to be transmitted, receiving pulses, and switching needed for actuation and pulsing in conjunction with digital logic implemented ahead of the clock generator, to generate variable clocks. In various embodiments, each FSD of the FMS can comprise a clock generator (e.g., clock generator 302) and the clock generator can be used to generate MOD frequencies for exciting a piezo crystal (i.e., a transducer), wherein a MOD frequency can refer to the different operating frequencies such as, for example, 1.151 MHz, 1.162 MHz, etc., of an FSD. For example, clock generator can excite a piezo crystal for generating ultrasound waves (or pulses/signals) that can be directed at a fetus, reflect off the fetus and return to the piezo crystal. For exciting the piezo crystal, the clock generator can generate a clock signal, wherein the clock signal is an electronic signal that can oscillate at a specific MOD frequency. The clock generator can provide a base frequency based on which a wave can be shaped and driven by a dedicated circuitry inside the FSD to drive the piezo crystal. Thereafter, the piezo crystal can convert the reflected ultrasound wave into electrical energy that can be processed during a signal processing stage.

Clock generator 302 can comprise crystal 304, wherein crystal 304 can be a quartz crystal. It is to be appreciated that the quartz crystal and the piezo crystal are different elements. As noted supra, the piezo crystal can be used to transmit and receive ultrasound waves but not for generating the clock used by clock generator 302 for generating the different frequencies, as discussed herein. Clock generator 302 can further comprise PLL A (fractional multiplier) 306, a fractional multiplier that can be a PLL for multiplying a crystal frequency by a value, X, and further dividing the result to generate a desired MOD frequency. Clock generator 302 can generate a MOD frequency (illustrated at 310), a second frequency (illustrated at 308) equal to 8×MOD frequency and a third frequency (illustrated at 312) equal to MOD frequency+200 Hz. The MOD frequency can be used to drive and actuate the piezo crystal in the FSD. The 8×MOD frequency can be a higher frequency generated by the clock generator and needed for driving the processor, and the 8×MOD frequency can be sent to the processor to drive the digital logic inside the processor. The MOD frequency+200 Hz frequency can be used for calibrating the tunable LC tank circuitry. It is to be appreciated that the frequencies and configuration described herein are exemplary and not specific. For example, the second frequency (illustrated at 308) can be Z×MOD frequency, wherein Z can be 8 or another numeric value and the third frequency (illustrated at 312) can be MOD frequency+Y Hz, wherein Y can be 200 or another numeric value. Similarly, the MOD frequency can be a multiple of the MOD frequency (illustrated at 310). As such, the MOD frequency can be used as a carrier wave, the 8×MOD frequency can be used to source the digital section, and the MOD frequency+200 Hz frequency can enable automatic calibration of the LC tank. Thus, the clock generator can be employed (e.g., by frequency generation component 108) to generate multiple MOD frequencies.

FIG. 4 illustrates a circuit diagram of an example, non-limiting tunable LC tank circuit 400 comprising large capacitance varactors in accordance with one or more embodiments described herein. One or more embodiments described with reference to FIG. 4 can be enabled by one or more components of system 100. Repetitive description of like elements and/or processes employed in respective embodiments is omitted for sake of brevity.

With continued reference to FIGS. 1 and 3, the various embodiments herein disclose a method in which an FSD can be calibrated to maximize gain at every frequency (thus ensuring tuning of a resonant frequency of the LC network). The corresponding DAC value can be stored in the FSD. For example, the variable frequency generator circuitry can use an attenuated shifted frequency to automate a calibration process for the tunable LC tank circuit, and wherein the FSD can be calibrated to maximize gain at the carrier frequency of the FSD, wherein the carrier frequency can be a frequency selected from the one or more different frequencies generated by the clock generator (variable frequency generator circuitry). Storage component 110 can store a DAC value corresponding to maximizing gain of the tunable LC tank circuit at the carrier frequency of the FSD. In various embodiments, storage component 110 can store multiple DAC values (or multiple values corresponding to another voltage control mechanism) on a single FSD because each frequency generated by the variable frequency generator circuitry can have a respective DAC value. Thus, all the DAC values corresponding to each of the one or more carrier frequencies generated in an FSD, after the calibration process, can be stored in the FSD. When the FSD is turned on, the FSD can choose or be signaled (e.g., by frequency generation component 108, a monitor) to select a channel of operation and configure non-limiting tunable LC tank circuit 400 (tunable LC tank circuit 400) to the DAC value for the corresponding FDM frequency. Clock generator 302 (e.g., the clock generation circuitry) can generate the same discrete frequency for modulation/demodulation.

As stated elsewhere herein, clock generator 302 can also be used (e.g., by frequency generation component 108) to generate a shifted frequency (e.g., a doppler shifted frequency) and driving the square wave after attenuating the square wave into the receive circuitry (tunable LC tank circuit 400 can allow only the first harmonic sine wave to pass through while higher order harmonics experience significant attenuation) can help automate the calibration process for tunable LC tank circuit 400 by changing the DAC voltage to maximize the amplitude of the shifted signal of interest at the ADC. Further, the resonant frequency of tunable LC tank circuit 400 can drift with change in temperature due to the variations in winding inductance and capacitance added by the varactors. The behavior of the resonant frequency can be characterized and compensated for to ensure consistent performance of tunable LC tank circuit 400 across various operating conditions. For example, in various embodiments, as the operating temperature of an FSD changes, the DAC value can also change to compensate for the LC tank's thermal characteristics.

An input to tunable LC tank circuit 400 can be an electrical signal received from the piezo crystal and generated by the piezo crystal by converting ultrasound waves reflected by a fetus into electrical energy, as illustrated by input 410. Tunable LC tank circuit 400 can comprise an inductor (LA) and a capacitor, wherein the inductor can be a simple inductor and the capacitor can be a simple capacitor. Tunable LC tank circuit 400 can further comprise large capacitance varactors DA, DB, DC, and DD, that can tune a resonant frequency of tunable LC tank circuit 400 to a carrier frequency of the FSD. Various embodiments herein can employ the large capacitance varactors given the lower frequencies of operation of FSDs described herein as compared to high frequency applications of varactors. Varactors are elements like diodes. However, varactors can have a tunable capacitance, wherein based on a biasing voltage, the capacitance of a varactor can be tuned. More specifically, the varactor network as illustrated in tunable LC tank circuit 400 can be used to balance the capacitances in tunable LC tank circuit 400 given the fluctuations in the biasing voltages due to the input signals in tunable LC tank circuit 400. In circuit 400, DA, DB, DC, and DD make up the balanced network/varactor network. In tunable LC tank circuit 400, the entire circuit below the horizontal line connecting the inductor and the mid-point (LNA_FRONTEND_OUT) can be considered a single capacitor. The capacitor of tunable LC tank circuit 400 can be split into multiple sections for fine-tuning the exact capacitance value. For example, the capacitance of tunable LC tank circuit 400 can be split into two parallel capacitances from two capacitors connected in parallel (capacitor CA illustrated at 402 and capacitor CB illustrated at 404), followed by capacitance from the varactors, and some additional capacitance from diodes of tunable LC tank circuit 400, located after the varactors. Capacitors CA and CB can be used as fixed capacitances to attain the tuned LC voltage while accommodating for the swing that can be delivered by the varactor network. Capacitors CC and CD can be used to isolate the bias voltage from the main signal line. The capacitance value of the varactors can be dynamically changed using a reverse bias voltage generated/adjusted by the DAC, such that tunable LC tank circuit 400 can be tuned to the carrier frequency being used by the FSD. It is to be appreciated that the configuration of tunable LC tank circuit 400 illustrated in FIG. 4 is exemplary, and the LC circuit discussed in one or more embodiments can have a different configuration.

The capacitance values from the two parallel capacitors (i.e., CA and CB) and the diodes (illustrated at 414) can be fixed values, and the varactors can generate variable capacitance. The use of a diode in tunable LC tank circuit can allow controlling the gain (by clamping) for large level signals such as the transmit pulse of the same transducer or crosstalk transmit signals from a different transducer. The diode can also add a fixed capacitance in parallel to the signal line. The fixed value capacitances can be used to provide a base value upon which the varactors can add capacitance to adjust the total value of all capacitances in parallel. In various embodiments, C0G capacitors can be chosen to maximize stability of capacitance values and a lower resistance inductor/lower leakage current diode can be used to minimize losses. Varactors can be introduced in tunable LC tank circuit 400 to precisely tune an FSD by tuning the varactors to generate a precise capacitance representative of the carrier frequency of the FSD. For example, when FSDs are manufactured, the respective capacitances on board the FSDs can vary from unit to unit due to presence of dust, amount of solder, etc. Varactors can also account for variations in the inductance of the inductor. A frequency of resonance/resonant frequency (f) of an FSD can be determine using equation 1.

Input 410 can enter the three capacitors including the two capacitors connected in parallel and the diodes of tunable LC tank circuit 400. Once the electrical signal represented by input 410 is tuned, the electrical signal can oscillate back and forth between the inductor-capacitor and the mid-point (LNA_FRONTEND_OUT illustrated at 412) of tunable LC tank circuit 400, and the electrical signal can become amplified. Thereafter, the amplified signal can proceed to subsequent amplification sections. In this manner, tunable LC tank circuit 400 can pre amplify the electrical signal. As such, the mid-point (LNA_FRONTEND_OUT) can proceed to the subsequent amplification sections such that by the time the signal leaves tunable LC tank circuit 400, unwanted signals not in the frequency band of the tuned LC circuit can become attenuated.

Figure 5:
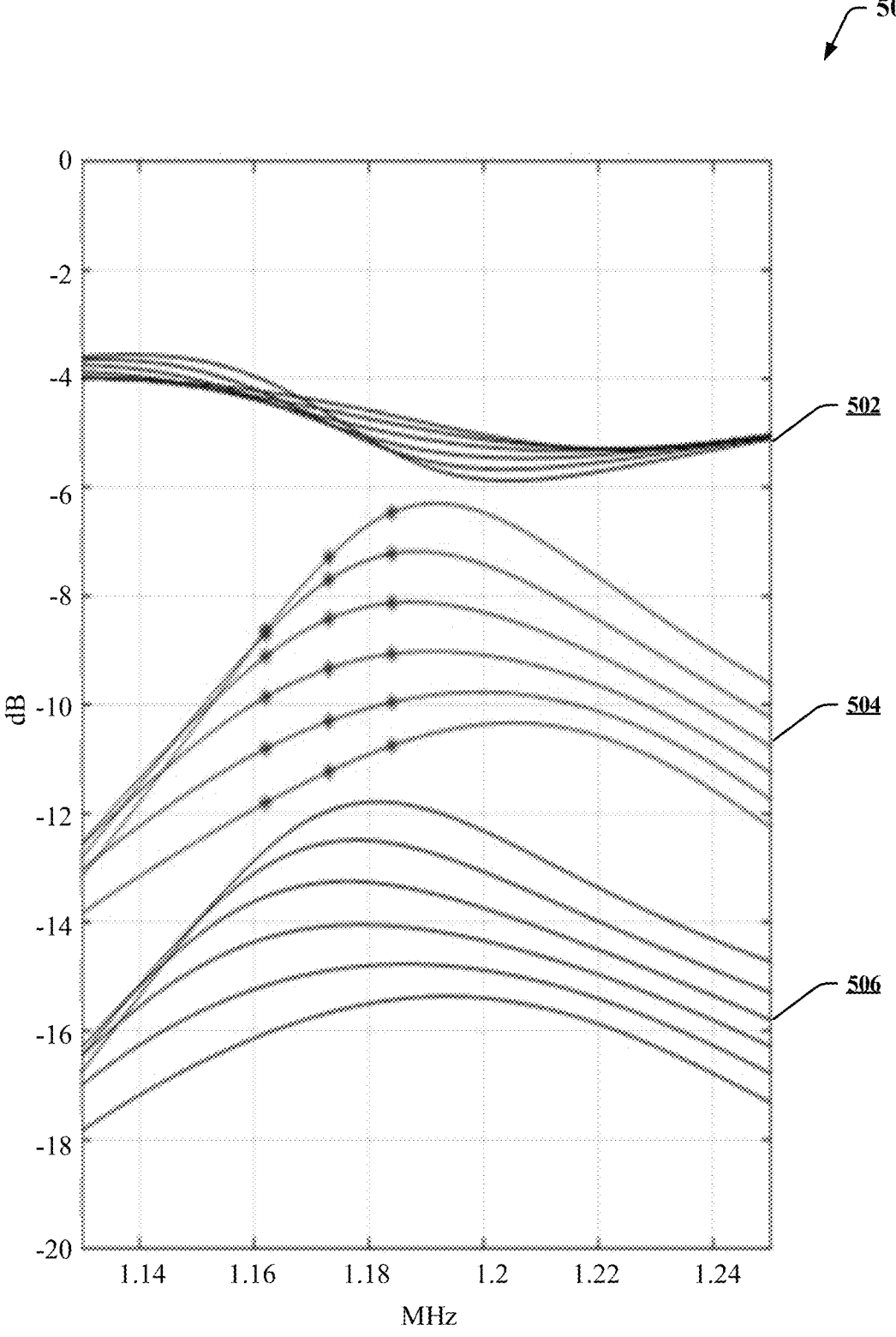
FIG. 5 illustrates an example, non-limiting graph of a finite element method (FEM) simulation in accordance with one or more embodiments described herein.

FIG. 5 illustrates an example, non-limiting graph 500 of an FEM simulation in accordance with one or more embodiments described herein. One or more embodiments described with reference to FIG. 5 can be enabled by one or more components of system 100. Repetitive description of like elements and/or processes employed in respective embodiments is omitted for sake of brevity.

With continued reference to FIGS. 1, 3 and 4, non-limiting graph 500 (graph 500) illustrates an FEM simulation of piezoelectric efficiency of a device, showing multiple options for FDM while ensuring maximum sensitivity. In various embodiments, piezo crystals (transducers) can be narrowband crystals. Various embodiments herein can employ narrowband transducers for transformational efficiency in an FMS. Narrowband transducers can work with great efficiencies at specific frequencies. For FDM, similar sensitivities can be required by MOD frequencies of FSDs. In graph 500, plot 502 can represent acoustic efficiencies and plot 506 can represent electrical efficiencies of FSDs. Plot 504 can be generated by combining plot 502 and plot 506, and plot 504 can show how sensitive an FSD can be to different frequencies. For example, the spots highlighted on plot 504 can indicate MOD frequencies (e.g., between 1.16 MHz and 1.2 MHz) to which the FSD can be sensitive. Each line of plot 502 can represent a characteristic of an FSD. Herein, all FSDs can have the same family of piezo electric crystal, and the variations in the characteristics of individual FSDs can arise from manufacturing process shortcomings and crystal tolerances. Plot 504 can indicate an overall efficiency of an FSD, directly indicating a sensitivity performance of the FSD. Plot 506 can represent electrical efficiencies of different transducers. For example, plot 506 illustrates five samples of electrical efficiencies plotted at different frequencies. It is evident from graph 500 that there can be multiple frequencies offering similar efficiencies, as indicated by the points highlighted on plot 504. There can be various possibilities for MOD frequencies and all extremes can be considered.

FIG. 6 illustrates a diagram of an example, non-limiting interference pattern 600 representative of crosstalk artefacts in accordance with one or more embodiments described herein. One or more embodiments described with reference to FIG. 6 can be enabled by one or more components of system 100. Repetitive description of like elements and/or processes employed in respective embodiments is omitted for sake of brevity.

With continued reference to FIG. 1, various embodiments herein can generate predictable outcomes from all crosstalk scenarios to selectively eliminate all artifacts and to ensure reliability of FMSs. This can be achieved by selecting specific excitation and reception schemes to avoid signal aliasing and to generate noises that are always modulated onto predictable 1 kHz harmonics that can be used to identify and eliminate the effects of crosstalk in the system. When signals transmitted by one FSD are directly received by another FSD, artefacts and interferences can be generated. For a scenario with n asynchronous FSDs being used on a single mother, the respective carrier frequencies of the FSDs need to be separated to prevent a frequency difference between any two FSDs from being a multiple of the PRR of either FSD, to avoid incidences of crosstalk and interferences in an FMS. It is to be appreciated that for coexistence of n FSDs using FDM on a single mother, the PRR p should be at least n kHz. Since the receive front end of an FSD can be designed for very small signals (with high amplification), the clock inaccuracies in both systems (e.g., FSDs) can generate minute harmonics that can become magnified and creep into the receive signal chain of an FSD. This can further result in generating predictable interference harmonics far outside the band of interest (15-300 Hz), that is, for every 1 kHz from 1 kHz to (p−1) kHz. The noises generated due to inaccuracies in the PRRs and in the MOD frequencies can become modulated (frequency modulation (FM)) onto these relatively higher frequency interference harmonics. As a result, the effects of frequency inaccuracies can be detected and controlled by finding and eliminating the 1 kHz repetition harmonics in the signal.

In various embodiments, separation component 112 can separate a MOD frequency of an FSD in an FMS such that a difference of MOD frequencies of the FSD and another FSD is not a multiple of a PRR of the other FSD. Separation component 112 can separate the respective carrier frequencies by (p×(p−1)−1) kHz (Equation 2), where p represents the PRR of the FSD in kHz. The harmonics and effects of the corresponding crosstalk can be eliminated by implementing a filter that can notch the harmonic frequencies and by implementing an AGC stage that can normalize signal amplitudes. For example, in various embodiments, signal processing component 114 can implement the AGC stage and the filter to selectively eliminate the predictable harmonics to eliminate crosstalk in the FMS, and the AGC stage can be implemented as a software, a hardware or a combination of the software and the hardware. Normalizing the signal amplitudes can remove extremely low frequencies created due to crosstalk, and a notch filter can be implemented every 1 kHz, wherein the notch filter can the clean the harmonics. AGC can be implemented (e.g., by signal processing component 114) as a firmware/signal processing software/algorithm (significantly after the tunable LC tank circuitry) and the filter can be implemented (e.g., by signal processing component 114) after the AGC to eliminate the 1 kHz, 2 kHz and 3 kHz harmonics that can interfere with fetal heart rate detection. The filter and the algorithm for AGC can both be implemented in a signal processing core in the microcontroller. The AGC can also be implemented as a hardware block.

In an example, in a triplet monitoring scenario with a PRR of 4 kHz, wherein the respective frequencies of three FSDs (with each FSDs monitoring one of three fetuses) can be separated by 11 kHz, the crosstalk can result in production of 1 kHz and 2 kHz artefacts. The noise introduced by the PRR errors and the inaccurate carrier frequencies can be frequency modulated onto the 1 kHz and 2 kHz signals. Thereafter, the AGC stage can be implemented to normalize the amplitudes for signal detection, and further filtration of the 1 kHz and 2 kHz signals can completely attenuate all the noises generated due to crosstalk. Non-limiting interference pattern 600 (interference pattern 600) can illustrate an example of crosstalk. Interference pattern 600 can illustrate a core fundamental frequency of a 1 kHz sine wave. Upon implementing AGC, interference pattern 600 can look like a flat band of a 1 kHz sine wave as opposed to the shape illustrated by interference pattern 600. More specifically, interference pattern 600 can illustrate an example of crosstalk artefacts made of lower frequencies riding on a 1 kHz sine wave. The interference illustrated by interference pattern 600 can occur between two FSDs operating at 1.151 MHz and 1.162 MHz at a PRR of 4 kHz. Interference pattern 600 can occur due to the frequency inaccuracies in the carrier waves and the MOD frequencies of FSDs. Applying the AGC stage and filtering the 1 kHz harmonics can result in an almost zero signal amplitude for either FHR or FMD detection, which can be insufficient amplitude to produce any audible noise or artefacts in the fetal parameters being monitored.

Effects of crosstalk in the FMS can be reduced by reducing the frequency inaccuracies of the clock sources used by the transducers. Using a high precision clock source for a commercial cost-effective FSD is not always economical. Embodiments disclosed herein can use a frequency calibration technique during manufacturing of a transducer, wherein the frequency calibration technique can be performed in a temperature-controlled environment given the influence of temperature deviations on quartz crystals. For each of the carrier frequencies, the calibration process can determine the inaccuracy in the input crystal which can be utilized to tune (e.g., by frequency generation component 108) the frequency generation circuitry to generate an accurate frequency output based on the inaccurate input clock or crystal. As stated elsewhere herein, the calibration can be a digital calibration performed (e.g., by frequency generation component 108) via a software.

Figure 7:
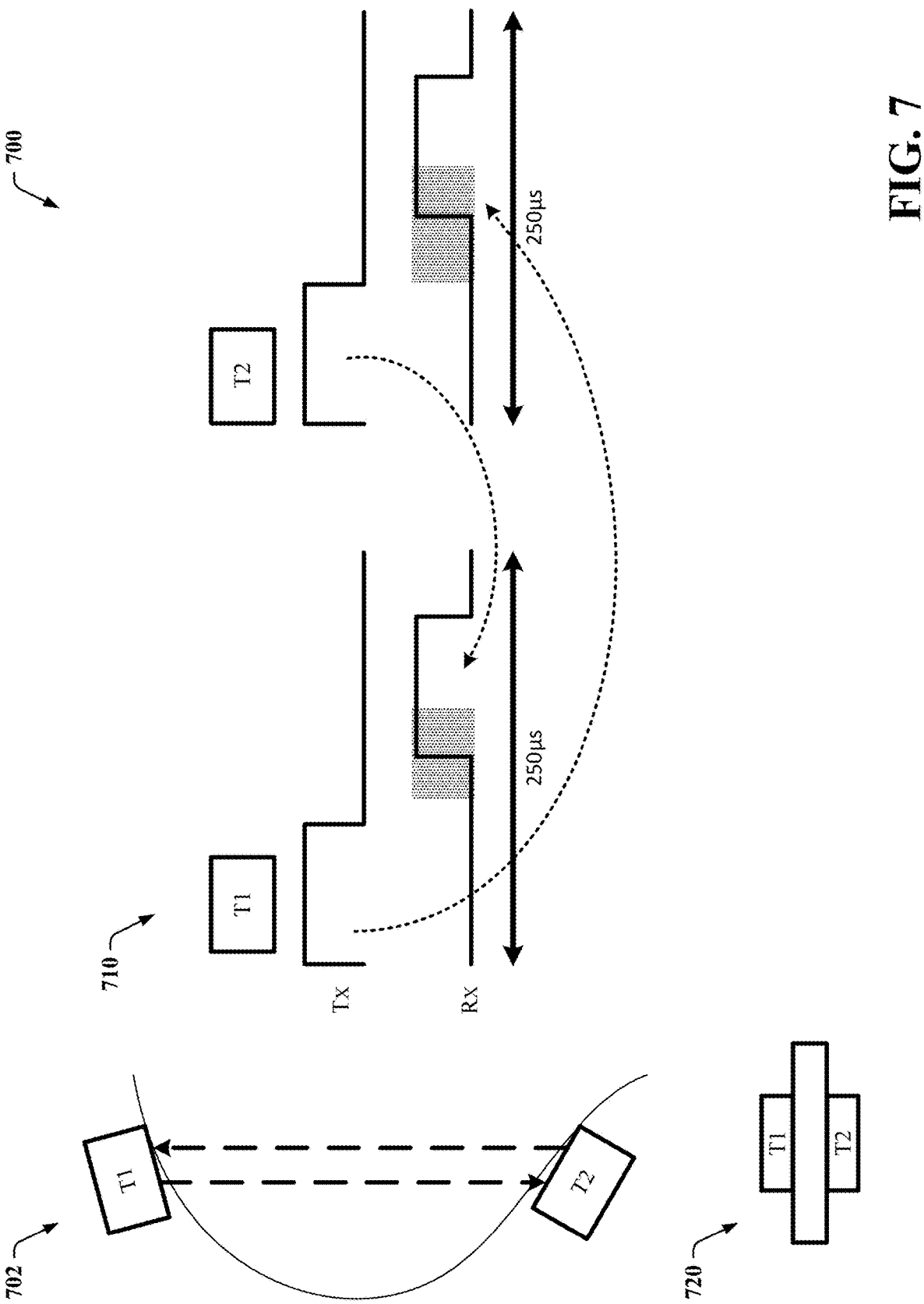
FIG. 7 illustrates diagrams of an example, non-limiting scenario that can generate crosstalk in an FMS in accordance with one or more embodiments described herein.

FIG. 7 illustrates diagrams of an example, non-limiting scenario 700 that can generate crosstalk in an FMS in accordance with one or more embodiments described herein. One or more embodiments described with reference to FIG. 7 can be enabled by one or more components of system 100. Repetitive description of like elements and/or processes employed in respective embodiments is omitted for sake of brevity.

Non-limiting scenario 700 (scenario 700) can be an example of a scenario wherein one or more embodiments discussed herein can be implemented to address frequency interactions and crosstalk in an FMS.

Positioning of FSDs for fetal monitoring can be performed by clinicians. For a clinician, looking at whether signal beams from FSDs are within the line of sight can be an impractical task. Illustrated at 702 is an example of a placement of FSDs for fetal monitoring that can generate crosstalk. Illustrated at 710 is an example of how the placement of FSDs illustrated at 702 can generate the crosstalk. At 710, the left portion of the diagram can illustrate the transmit period (TX) and the receive period (RX) of FSD T1, and the right portion of the diagram can illustrate the transmit period (TX) and the receive period (RX) of FSD T2. In this scenario, the transmitted signal from sensor T1 can be received by T2 during the receive period of T2 and can become demodulated, as illustrated by the dashed arrow from T1 to T2. Likewise, the transmitted signal from sensor T2 can be received by T1 during the receive period of T1 and can become demodulated, as illustrated by the dashed arrow from T2 to T1. In this regard, illustrated at 720 is a diagram of an experimental set up performed for monitoring crosstalk using FSDs T1 and T2. The experiments were performed on a Phantom and the results are described with reference to FIG. 8.

FIG. 8 illustrates diagrams of example, non-limiting interference patterns 800 and 810 representative of crosstalk artefacts in accordance with one or more embodiments described herein. One or more embodiments described with reference to FIG. 8 can be enabled by one or more components of system 100. Repetitive description of like elements and/or processes employed in respective embodiments is omitted for sake of brevity.

With continued reference to at least FIG. 7, FIG. 8 illustrates results corresponding to the experimental setup illustrated at 720 of FIG. 7, wherein FSDs T1 and T2 were placed directly across each other and the processed signal at the input to the ADC at either FSD was observed. In a scenario, both, T1 and T2, had a pulse repetition period of about 250 μs. T1 had a MOD frequency of 1.15097613 MHz and a PRR of 3.999917 kHz, and T2 had a MOD frequency of 1.16197836 MHz and a PRR of 3.9992551 kHz. Accordingly, the interference pattern illustrated at 800 corresponds to a frequency difference generated based on Equation 4. The interference pattern at 800 can show a sine wave repeated at a third harmonic of 2.3 Hz. The sliver, indicated at 802 on the interference pattern illustrated at 800, can be zoomed in to reveal the interference pattern at 804. Similarly, the interference pattern illustrated at 810 corresponds to the frequency difference generated based on Equation 5. The interference pattern at 810 can show a slow-moving pattern that repeats every 8 mHz.

$\Delta F = \|MOD_{T1} - MOD_{T2}\| - 11$ KHz$| = \sim 2.3$ Hz, wherein $MOD_{T1}$ represents the MOD frequency of $T1$ (1.15097613 MHz in the experimental scenario) and $MOD_{T2}$ represents the MOD frequency of $T2$ (1.16197836 MHz in the experimental scenario).     Equation 4:

$|PRR_{T1} - PRR_{T2}| = \sim 8$ mHz, wherein $PRR_{T1}$ represents the $PRR$ of $T1$ (3.999917 kHz in the experimental scenario) and $PRR_{T2}$ represents the $PRR$ of $T2$ (3.9992551 kHz in the experimental scenario).     Equation 5:

Based on the above discussion, it can be observed that every frequency involved in pulse formation can produce crosstalk effects. Separating (e.g., by separation component 112) MOD frequencies of FSDs to generate predictable harmonics and applying AGC and filters (e.g., by signal processing component 114) to eliminate the predictable harmonics can eliminate crosstalk in an FMS.

Figure 9:
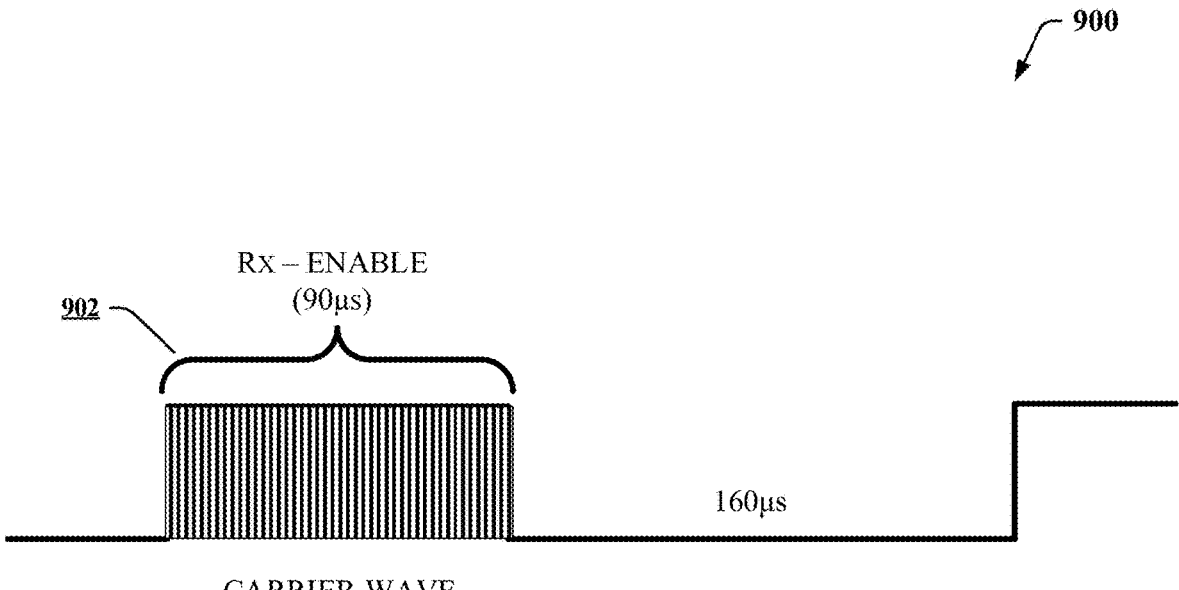
FIG. 9 illustrates a diagram of an example, non-limiting carrier wave in accordance with one or more embodiments described herein.

FIG. 9 illustrates a diagram of an example, non-limiting carrier wave 900 in accordance with one or more embodiments described herein. One or more embodiments described with reference to FIG. 9 can be enabled by one or more components of system 100. Repetitive description of like elements and/or processes employed in respective embodiments is omitted for sake of brevity.

With continued reference to at least FIGS. 6-8, FIG. 9 describes ultrasound (ULS) aliasing and demodulation of signals in an FMS. Non-limiting carrier wave 900 (carrier wave 900) illustrates a pulse repetition period for an FSD. At 902, carrier wave 900 can indicate the receive period (RX-Enable) for the FSD, and the receive period can have a duration of 90 μs. The transmit period (TX) for the FSD can be indicated by the flat portion of the carrier wave 900, and the transmit period can have a duration of 160 μs. The FSD can operate by looking for a doppler shift and demodulating. For example, the FSD can have a carrier frequency of 1.140 MHz (a cable running at 1.140000 MHz), and the FSD can experience crosstalk from a first sensor (FSD) operating at 1.151 MHz and a second sensor (FSD) operating at 1.162 MHz. Due to crosstalk, the 1.151 MHz signal from the first sensor and the 1.162 MHz signal from the second sensor can get demodulated at 1.140 MHz, within the RX-Enable period of the FSD. Demodulation can mean subtraction. Thus, the demodulation can result in a difference of 11 kHz between the FSD and the first sensor and a difference of 22 kHz between the FSD and the second sensor.

The 11 kHz and 22 kHz frequencies can be received by the FSD within the Rx-Enable period (90 μs), after demodulation. Since the FSD considered herein has a pulse repetition period of 250 μs (90 μs+160 μs), according to Equation 3, the PRR of the FSD can be 4 kHz. In other words, the FSD can sample signals at 4 kHz. In this scenario, the 11 kHz signal sampled at 4 kHz can generate an output of 1 kHz. That is, within the RX-Enable period, there can exist an 11 kHz signal that can occur only once every 250 μs (i.e., only during the receive period of the FSD). In effect, the demodulation itself represents a sampling at 4 kHz. Thus, the 11 kHz signal sampled at 4 kHz can imply sampling the 11 kHz signal at a sampling rate of 4 kHz, which can generate an output of 1 kHz (harmonics) that can be used to eliminate crosstalk. Similarly, the 22 kHz signal sampled at 4 kHz can generate an output of 2 kHz (harmonics), because based on the Nyquist theory, the smallest frequency that can be achieved is half of the sampling frequency. Thus, for a sampling rate (PRR) of 4 kHz, the Nyquist frequency is 2 kHz and for a sampling rate of 2 kHz, the Nyquist frequency is 1 kHz. Since the outputs generated can be 1 kHz and 2 kHz, the shift of 100-300 Hz observed can add/subtract to this, thereby ensuring that the signals never enter the zero (0) Hz to 300 Hz band of interest for fetal heart rate monitoring.

In general, the signals of interest for fetal monitoring (fetal heart rate monitoring or fetal movement monitoring or similar) are typically in the 15 Hz to 300 Hz range. Thus, for a doppler shifted system, the bandwidth of the signals can be about 600 Hz (i.e., a 300 Hz in either direction from the nominal carrier frequency). Given this bandwidth of the signals of interest, the PRR and the carrier frequencies of FSDs are preferable to be in whole multiples of 1 kHz because using fractional multiples can lead to interference and false pickup. For example, considering two FSDs, namely, T1 and T2, both operating at a PRR of 3 kHz, wherein T2 can be operating at a carrier frequency higher than T1 by 3.5 kHz, any positive doppler shift on a T1 signal can be picked up by T2, and any negative doppler shift on T2 can be picked up by T1. In the case of T2 picking up a T1 signal, the separation between the signal (with 200 Hz doppler shift) and the T2 frequency can be 3.3 kHz (3.5 kHz–200 Hz). Due to the PRR being 3 kHz, T2 can perceive the signal as a 300 Hz shift (3.3 kHz=3 kHz+300 Hz) per Nyquist theory, bringing the signal into the band of interest. If the difference is 4 kHz, then the T2 frequency can be 3.8 kHz (4 kHz–200 Hz). With the PRR of 3 kHz, per Nyquist theory, T2 can perceive the signal as an 800 Hz shift (3.8 kHz=3 kHz+800 Hz), outside the band of interest.

The following example can further highlight how the various embodiments disclosed herein can handle strong reflected signals with a doppler shift. It should be noted that this embodiment can be implemented only to handle large signals since the tunable LC tank circuit can account for smaller signals. In an FMS, sensors other than an FSD transmitting a signal can also receive the signal transmitted by the FSD and a corresponding signal reflected from a fetus being monitored by the FSD. Various embodiments herein can prevent direct and reflected signals from one or more FSDs, received by an FSD, from entering the signal chain of the FSD. Consider, for example, a 200 Hz doppler shifted signal on a 1.151 MHz carrier signal from the first sensor and a 1.162 MHz carrier signal from the second sensor. In this scenario, the reflected signal from the first sensor can have a frequency of 1.151200 MHz (positive (+) 200 Hz shift) and the reflected signal from the second signal can have a frequency of 1.162200 MHz (positive (+) 200 Hz shift). In other words, the first sensor can transmit a signal at 1.151 MHz that can be reflected by a fetus and doppler shifted by 200 Hz, wherein the frequency of the reflected signal can be 1.151200 MHz due to the doppler shift.

With the same logic, the 1.162 MHz signal from the second sensor can be doppler shifted by 200 Hz, resulting in a reflected signal of 1.162200 MHz. The reflected signals of 1.151200 MHz and 1.162200 MHz can enter the receive period of the FSD operating at 1.140 MHz (in addition to entering the first sensor and the second sensor, respectively), resulting in respective demodulated signals of 11200 Hz and 22200 Hz. According to Nyquist theory, the 11200 Hz signal can result in an output of 800 Hz, and the 22200 Hz signal can result in an output of 1800 Hz. The 800 Hz output and the 1800 Hz output can be outside of the band of interest of frequencies and can be eliminated (e.g., by signal processing component 114), and the doppler shifted artefacts can also be eliminated (e.g., by signal processing component 114). In this scenario, the reflect signals already being small, the tunable LC tank circuit can account for most of the reflected signals. Likewise, a reflected signal of 1.150800 MHz (negative (–) 200 Hz shift) from an FSD, entering the FSD operating at 1.140 MHz, can be demodulated to generate a frequency difference of 10800 Hz and an output of 1200 Hz, and a reflected signal of 1.161800 MHz (negative (–) 200 Hz shift) from an FSD, entering the FSD operating at 1.140 MHz, can be demodulated to generate a frequency difference of 21800 Hz and an output of 1800 Hz. As before, the 1200 Hz and 1800 Hz outputs can be outside the 0 Hz-300 Hz band of interest of frequencies, and the FSD operating at 1.140 MHz can avoid detecting doppler shifted frequencies from a different FSD.

The following discussion described how sampling rate can cause aliasing. If the FSD with the carrier frequency of 1.140 kHz has a PRR/sampling rate of 2 kHz, a frequency of 1.151 MHz without a doppler shift, demodulated at 1.140 MHz, can result in a frequency difference of 11 kHz and an output of 1 kHz per the Nyquist theory. Similarly, a frequency of 1.162 MHz without a doppler shift, demodulated at 1.140 MHz, can result in a frequency difference of 22 kHz and an output of 0 kHz per the Nyquist theory. Further, for a PRR of 2 kHz, a doppler shifted frequency of 1.151200 MHz (positive doppler shift) demodulated at 1.140 MHz can generate a frequency difference of 11200 Hz and an output of 800 Hz, a doppler shifted frequency of 1.150800 MHz (negative doppler shift) demodulated at 1.140 MHz can generate a frequency difference of 10800 Hz and an output of 800 Hz, a doppler shifted frequency of 1.162200 MHz (positive doppler shift) demodulated at 1.140 MHz can generate a frequency difference of 22200 Hz and an output of 200 Hz, and a doppler shifted frequency of 1.161800 MHz (negative doppler shift) demodulated at 1.140 MHz can generate a frequency difference of 21800 Hz and an output of 200 Hz. In the four scenarios presented, the 200 Hz frequencies can be detected within the FHR band/band of interest and can become amplified by the main filter, thereby resulting in crosstalk. Table 1 lists different frequencies sampled at 4 kHz and 2 kHz sampling rates and the corresponding outputs.

TABLE 1

| Input signal frequency | Sampling rate | Output |
|---|---|---|
| 0 kHz | 2 kHz | 0 Hz |
| 1 kHz | 2 kHz | 1 kHz |
| 2 kHz | 2 kHz | 0 Hz |
| 3 kHz | 2 kHz | 1 kHz |
| 4 kHz | 2 kHz | 0 Hz |
| 5 kHz | 2 kHz | 1 kHz |
| 11200 Hz | 2 kHz | 800 Hz |
| 21800 Hz | 2 kHz | 200 Hz |

Figure 10:
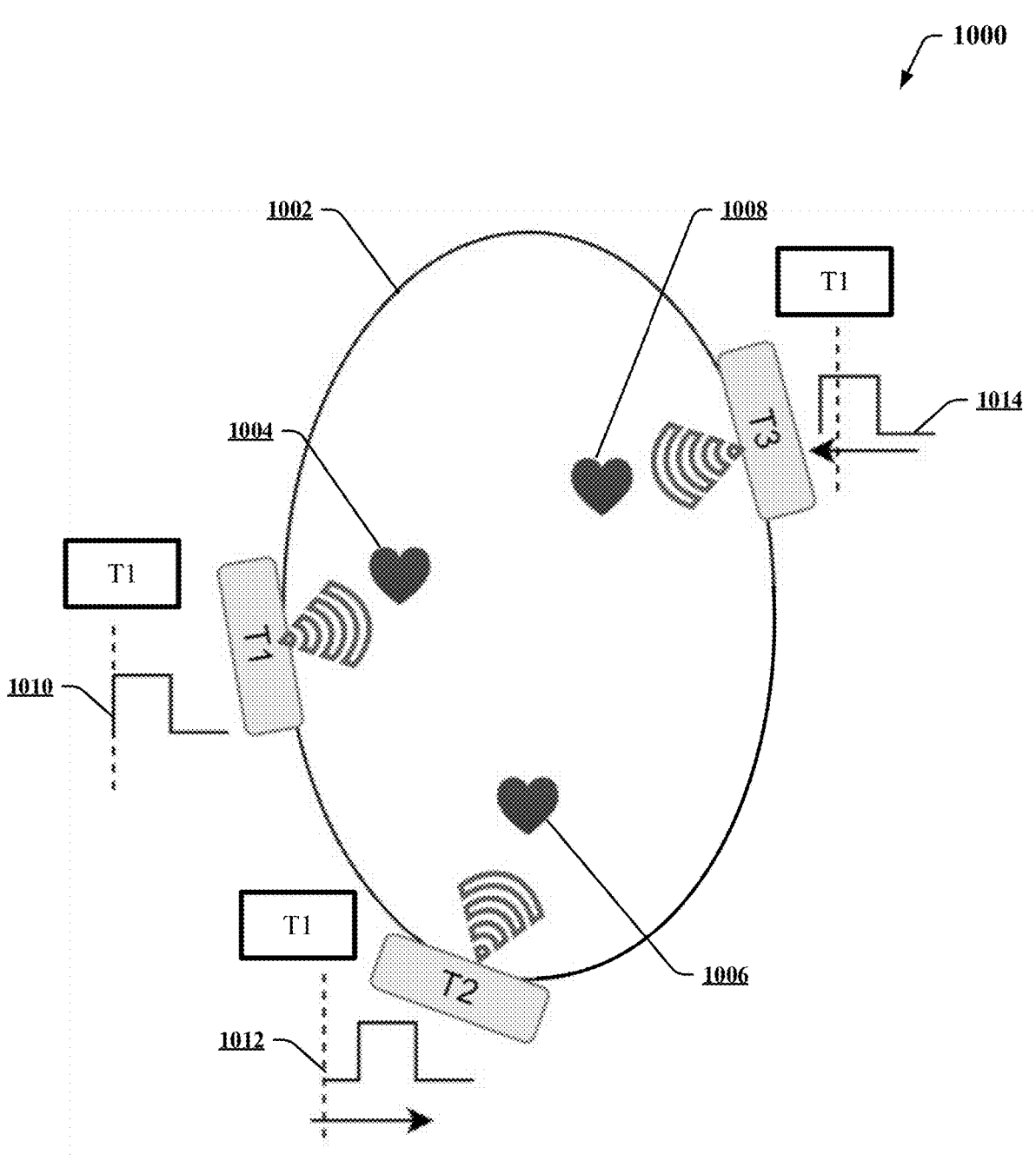
FIG. 10 illustrates a diagram of an example, non-limiting scenario of three FSDs positioned on a pregnant woman for monitoring fetal parameters (heartbeats of triplets or gross body movement) in accordance with one or more embodiments described herein.

FIG. 10 illustrates a diagram of an example, non-limiting scenario 1000 of three FSDs positioned on a pregnant woman for monitoring fetal parameters (heartbeats of triplets or gross body movement) in accordance with one or more embodiments described herein. One or more embodiments described with reference to FIG. 10 can be enabled by one or more components of system 100. Repetitive description of like elements and/or processes employed in respective embodiments is omitted for sake of brevity.

Various embodiments herein can enable PRR synchronization to ensure that large signal transmit pulses of one FSD in an FMS do not get demodulated by another FSD, thereby eliminating all artefacts in the FSDs. Independent FSDs having respective free running clocks can indicate a high likelihood that the respective free running clocks determining the timing of pulses for the FSDs can be slightly unsynchronized with respect to one another. Such a situation can indicate that the respective PRRs of the FSDs can be unsynchronized, and that the transmit and receive pulses can move with respect to each other on either of the FSDs in a crosstalk scenario. For example, a transmit pulse can reach the receive section of another FSD. The relative shift/movement of pulse patterns generated by the FSDs can result in crosstalk components (at difference of their PRR frequencies) and corresponding harmonics. MOD frequency errors can also result in crosstalk, specifically in extremely large signals. This can happen mainly due to harmonics generated when differences in frequencies are not perfect values (e.g., delta (frequency difference)±few Hz instead of 11 kHz, 22 kHz, etc.) that when sampled at 4 kHz can show harmonics at high amplitude inputs.

With continued reference to FIG. 1, synchronization component 116 can perform a periodic PRR synchronization to prevent demodulation of ultrasound signals generated by an FSD by respective carrier frequencies generated by additional FSDs in the FMS, to prevent crosstalk in the FMS. It is to be appreciated that demodulation of ultrasound signals generated by an FSD can occur after the ultrasound signals from the FSD being received by another FSD, converted to electrical signals by the transducer (piezo crystal) of the other FSD, and processed by the tunable LC tank circuitry of the other FSD. Non-limiting scenario 1000 can illustrate an FMS of three FSDs, namely, T1, T2 and T3, positioned on surface 1002 (i.e., the abdomen of a pregnant woman). FSD T1 can be employed to monitor fetal heartbeat 1004, FSD T2 can be employed to monitor fetal heartbeat 1006, and FSD T3 can be employed to monitor fetal heartbeat 1008. Due to clock differences between the FSDs, each of the three FSDs can have different PRRs. For example, with respect to the transmit pulse 1010 of FSD T1, the transmit pulses 1012 and 1014 of FSD T2 and FSD T3, respectively, can appear to move due to the differing PRRs, when viewed with reference to the dotted vertical lines. In this case, synchronization component 116 can perform a period PRR synchronization to ensure that the three FSDs can transmit pulses at the same PRR, which can prevent the generation of one kind of lower frequency noise during crosstalk. Synchronization component 116 can synchronize respective PRRs of FSDs T1, T2 and T3 in the FMS such that the respective PRRs of FSDs T1, T2 and T3 can remain synchronized even in case of a minor offset in MOD frequencies generated by respective clock generators of the three FSDs. In an embodiment, synchronization component 116 can synchronize transmit (Tx) pulses of FSDs T1, T2 and T3 regardless of there being any difference in the respective PRRs of the FSDs.

More specifically, synchronization component 116 can perform a periodic synchronization of the pulse patterns of FSDs T1, T2 and T3. For example, a monitoring system or a predetermined main FSD can transmit a slow yet very low jitter periodic ping to the FSDs to synchronize pulse patterns and PRRs of the three FSDs to reduce the artefacts, as discussed above. The periodic synchronization can be performed at a rate much lower than that of the PRRs but at least greater than a frequency difference between the PRRs. Doing so can reset the transmission before an entire cycle of window overlap is completed. That is, long before the Tx pulse of an FSD can overlap an entire pulse repetition period, synchronization component 116 can synchronize (periodically, only once in a while) the beginning of the transmit period of the FSD with respect to another FSD or a central hub to bring the start of the transmit period back to the original position and cut back on the drift. The frequency of performing the synchronization can be dictated by the maximum possible frequency offsets between any two sensors, and the frequency can be much higher than a frequency difference offset from an ideal expected difference. The PRR synchronization can maintain the respective transmit pulses (Txs) and receive pulses (Rxs) of FSDs from drifting across each other substantially to prevent creation of any crosstalk via low frequency harmonics without changing the PRR of an FSD. The PRR synchronization can prevent the generation of lower frequency noise during crosstalk. Generally, the difference in PRRs can be in single digit frequencies (Hz) or much lower (e.g., in mHz). By synchronizing the respective PRRs, one of the sources for crosstalk induced noise can be avoided. The ability of a system (e.g., an FMS) to synchronize in the case of wireless FSDs can also enable the possibility of a TDM implementation. In other embodiments, the PRR synchronization technique can be implemented alongside the AGC stage with filters for eliminating the crosstalk.

FIG. 11 illustrates diagrams of example, non-limiting scenarios 1100 and 1120 showing a synchronization of pulse patterns generated by FSDs positioned on a pregnant woman for monitoring fetal parameters (heartbeats of triplets or gross body movement) in accordance with one or more embodiments described herein. One or more embodiments described with reference to FIG. 11 can be enabled by one or more components of system 100. Repetitive description of like elements and/or processes employed in respective embodiments is omitted for sake of brevity.

With continued reference to FIG. 10, the periodic PRR synchronization can be performed by using a monitor to generate a ping in real time or by using electrodes and a main FSD to transmit to the additional FSDs. For example, a monitor can send signals to multiple FSDs of the FMS or the FSDs can operate in a peer-to-peer fashion for the synchronizing. For example, in an embodiment, synchronization component 116 can synchronize respective PRRs of the three FSDs by using a main hub or monitor that can act as a main device for controlling the FSDs of the FMS and that can send wireless signals in real time to the FSDs. In another embodiment, synchronization component 116 can synchronize respective PRRs of the three FSDs by using a main FSD/sensor that can wirelessly control other FSDs in the FMS and that can transmit signals (e.g., high frequency low-current signals) to additional FSDs in the FMS. The synchronization of the PRRs can be performed wirelessly, or through wired connections (e.g., wires).

Non-limiting scenario 1100 (scenario 1100) illustrates PRR synchronization of FSDs T1, T2 and T3 performed by hub 1102 by generating and transmitting a wireless ping in real time to the three FSDs, wherein hub 1102 can be a main hub that can control FSDs T1, T2 and T3. The real time wireless ping can be used as an interrupt to realign the transmit periods of the three FSDs. The transmit periods can also be realigned by using the human body as an antenna technology to reduce power requirements. Non-limiting scenario 1120 (scenario 1120) illustrates wireless PRR synchronization of FSDs T1, T2 and T3 performed by using electrodes and FSD 1122 (e.g., FSD T1) to transmit signals across surface 1002 such that the same signal can be picked up by the other FSDs (e.g., T2 and T3) on surface 1002 and used as an interrupt to realign pulses transmitted by the three FSDs. In various embodiments, the signals transmitted by FSD 1122 can be high-frequency low-current signals. Scenario 1100 and scenario 1120 illustrate wireless synchronization of pulse patterns (and thereby, PRRs) for FSDs T1, T2 and T3, as shown by the synchronized transmit pulses 1010, 1012 and 1014. In various embodiments, the PRR synchronization can be wired or wireless.

In some embodiments, the PRR synchronization can be implemented without implementing the AGC stage (i.e., by using only the filters) after separating the respective MOD frequencies of FSDs T1, T2 and T3 to generate the predictable harmonics. In other embodiments, the PRR synchronization technique can be implemented alongside the AGC stage with filters for eliminating the crosstalk.

Figure 12:
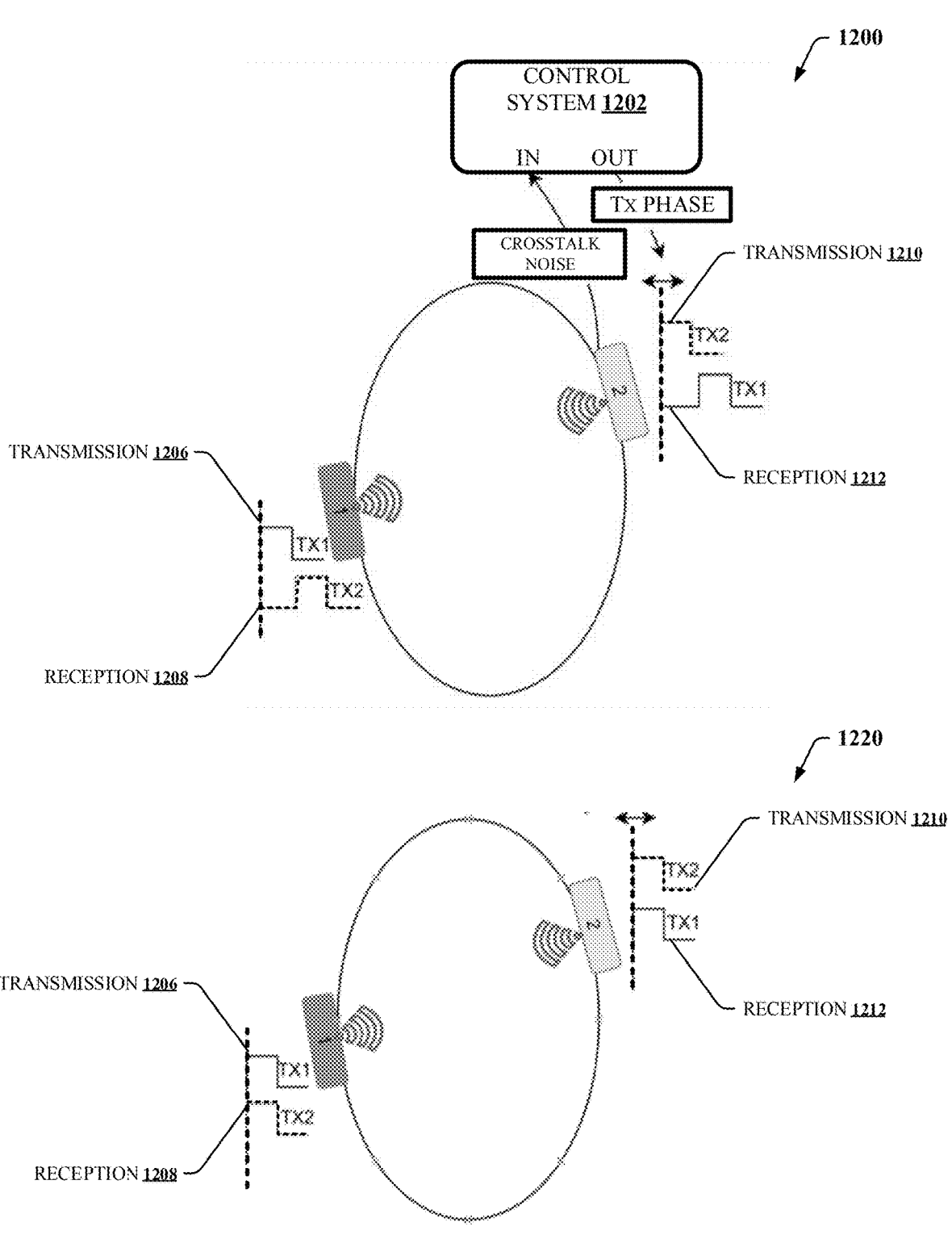
FIG. 12 illustrates diagrams of example, non-limiting scenarios showing a control system that can phase shift the start of a TX enable period of an FSD to eliminate the generation of crosstalk artefacts in an FMS in accordance with one or more embodiments described herein.

FIG. 12 illustrates diagrams of example, non-limiting scenarios 1200 and 1220 showing a control system that can phase shift the start of a TX enable period of a transducer to eliminate the generation of crosstalk artefacts in an FMS in accordance with one or more embodiments described herein. One or more embodiments described with reference to FIG. 12 can be enabled by one or more components of system 100. Repetitive description of like elements and/or processes employed in respective embodiments is omitted for sake of brevity.

Various embodiments herein can enable PRR synchronization to ensure that large signal transmit pulses of one FSD in an FMS do not get demodulated by another FSD, thereby eliminating all artefacts in the FSDs. In various embodiments herein, crosstalk can completely be avoided in an FMS by attacking the cause of the crosstalk. For example, if the transmit pulses of FSDs (i.e., signals transmitted by transducers) can overlap or the transmit pulses can be prevented from entering each other's receive periods, a possibility of the signals becoming demodulated can be avoided, which can further eliminate chances of any harmonics creeping in the FMS. Such a situation can also lead to lesser acoustic interference in the small signals. The travel time of ultrasound signals through the tissues of the abdomen can be high enough to warrant the need to factor in/account for a distance travelled by the transmit pulses, which can directly affect whether a pulse falls into a receive period (completely or partially). However, tracking the precise travel time of the pulse down to the microsecond can be challenging to accomplish and can depend on the relative positions of the FSDs on the abdomen.

Non-limiting scenario 1200 (scenario 1200) illustrates a fetal monitoring scenario wherein FSD 1 can be positioned directly across from FSD 2 on the abdomen of a pregnant woman. In FIG. 12, transmission 1206 (solid line) can represent a signal transmitted (TX1) by FSD 1 and reception 1208 (dashed line) can represent a signal received (TX2) by FSD 1. Similarly, transmission 1210 (dashed line) can represent a signal transmitted (TX2) by FSD 2 and reception 1212 (solid line) can represent a signal received (TX1) by FSD 2. A signal transmitted from FSD 2 can enter the reception period of FSD 1, and vice versa. The reception period of an FSD can refer to the period during which the FSD can expect to receive a reflected signal, after the transducer of the FSD has transmitted a signal. Thus, TX2 can represent the signal transmitted by FSD 2 and received by FSD 1 during the reception period of FSD 1, and TX1 can represent the signal transmitted by FSD 1 and received by FSD 2 during the reception period of FSD 2. In scenario 1200, FSD 1 can receive TX2 as well as a reflected signal (not illustrated in FIG. 12) corresponding to the signal transmitted by the FSD 1 (TX1). The strength of TX2 can be high due to the signal from FSD 2 being directly received by FSD 1, and scenario 1200 can generate 1 kHz, 2 kHz, 3 kHz, etc. harmonics. At the same time, FSD 2 can receive TX1 and a reflected signal (not illustrated in FIG. 12) corresponding to the signal transmitted by FSD 2 (TX2).

In various embodiments, synchronization component 116 can perform a pulse phase synchronization to shift a phase of the TX2 signal to prevent the TX2 signal from entering the receive period of FSD 1 located directly across from FSD 2. Synchronization component 116 can perform a pulse phase synchronization via control system 1202. For example, FSD 2 can be operatively coupled to control system 1202 and FSD 1 can operate without being coupled to control system 1202. Control system 1202 can measure an amount of harmonics being generated by FSD 2 at FSD1, and control system 1202 can gradually phase shift the TX2 signal transmitted by FSD 2, which can cause the TX2 signal to overlap with the TX1 signal. As a result, TX1 can become aligned with TX2, and prevent TX2 from entering the reception period of FSD 1.

More specifically, synchronization component 116 can eliminate the generation of crosstalk artefacts in an FDM system by using control system 1202 to detect the harmonics generated (every 1 kHz from ((p−1) kHz to 1 kHz), and phase shifting already synchronized PRRs of FSDs (e.g., FSDs 1 and 2). In this embodiment, an FSD with the highest amount of crosstalk components can act as the main FSD in an FMS, and the other FSDs can phase shift the respective starts of the respective TX enable periods of the other FSDs with respect to the main FSD. The phase shifting can be performed until there are no more crosstalk components remaining in any of the FSDs. As a result, for FSDs transmitting signals into each other across the abdomen of the mother (e.g., FSDs 1 and 2), the transmit pulses (e.g., TX1 and TX2) of the FSDs can be shifted in time to prevent a transmit pulse of one FSD from entering the reception period/receive window of the other FSD, thereby completely avoiding all possible crosstalk in the FMS. Implementing the embodiments discussed herein can indirectly take into consideration the travel times of the ultrasound transmit pulses from FSDs 1 and 2 across the abdominal tissues and resulting overlap location.

Thus, control system 1202 can shift the phase of a signal from FSD 2 to align the TX2 signal with the TX1 signal to prevent the TX2 signal from entering the receive period of FSD 1. Aligning TX2 with TX1 can also prevent the TX1 signal from entering the receive period of FSD 2. Such a technique can eliminate the need to remove crosstalk. Additionally, during crosstalk, a reflected signal (e.g., a signal reflected from a fetus) received by a transducer can sometimes be very weak, and in this case, a direct signal (e.g., TX1 or TX2) received by the transducer from another transducer, in addition to the reflected signal, can saturate the reflected signal. For example, in scenario 1200, the reflected signal corresponding to TX1 can become lost even if crosstalk is eliminated (e.g., by signal processing as described elsewhere herein). Phase shifting signals as described above, can prevent saturation of the reflected signal, and improve reception sensitivity of FSDs. That is, aligning the respective signals transmitted by the FSDs can prevent any large signals from flooding the respective receive chains of either FSD during their respective reception periods. This can allow a larger amount of voltage range to be available for a transducer to receive a reflected signal and amplify the reflected signal, for example, as compared to the scenario wherein a transducer can receive both, the reflected signal, and a transmitted signal from another transducer. Non-limiting scenario 1220 (scenario 1220) can illustrate the TX2 signal phase shifted until artefacts at either FSD have come down to zero. This can indicate that the transmits TX1 and TX2 can be overlapping and the respective travel times of the TX1 and TX2 waves can be compensated for across the abdomen of the pregnant woman.

FIG. 13 illustrates a flow diagram of an example, non-limiting method 1300 that can enable multiple FSD coexistence in an FMS in accordance with one or more embodiments described herein. One or more embodiments described with reference to FIG. 13 can be enabled by one or more components of system 100. Repetitive description of like elements and/or processes employed in respective embodiments is omitted for sake of brevity.

At 1302, the non-limiting method 1300 can comprise generating (e.g., by frequency generation component 108), by a device operatively coupled to a processor, using a variable frequency generator circuitry, electronic signals at one or more different frequencies in at least one FSD of an FMS, wherein the at least one FSD can dynamically adjust a transmit voltage of the at least one FSD to maintain one acoustic power value at the one or more different frequencies. At 1302, the non-limiting method 1300 can further comprise tuning, by the device, a resonant frequency of a tunable LC tank circuit comprised in the at least one FSD to a carrier frequency of the at least one FSD, wherein the carrier frequency can be a frequency selected from the one or more different frequencies, wherein the tunable LC tank circuit can comprise large capacitance varactors that perform the tuning, and wherein tuning the resonant frequency of the tunable LC tank circuit to the carrier frequency of the at least one FSD can comprise using, by the device, a DAC to adjust biasing voltages of a balanced varactor network to dynamically change a capacitance value of the large capacitance varactors. In some embodiments, tuning the resonant frequency of the tunable LC tank circuit to the carrier frequency of the at least one FSD can comprise using a voltage control mechanism other than a DAC, wherein the voltage control mechanism can be a resistor divider network, a DC regulator (that can generate a DC regulated voltage), or another type of voltage control mechanism.

At 1304, the non-limiting method 1300 can comprise separating (e.g., by separation component 112), by the device, respective carrier frequencies of the plurality of FSDs in the FMS such that a frequency difference between carrier frequencies of any two FSDs is not a multiple of a PRR of either FSD, wherein separating the respective carrier frequencies of the plurality of FSDs can generate predictable harmonics during crosstalk in the FMS.

At 1306, the non-limiting method 1300 can comprise implementing (e.g., by signal processing component 114), by the device, an AGC stage and a filter to selectively eliminate the predictable harmonics to eliminate crosstalk in the FMS, wherein the automatic gain control stage can be implemented as a software, a hardware or a combination of the software and the hardware.

At 1308, the non-limiting method 1300 can comprise performing (e.g., by synchronization component 116), by the device, a periodic PRR synchronization to synchronize a start of a transmit period of the at least one FSD with respective starts of transmit periods of one or more additional FSDs in the FMS to prevent ultrasound signals generated by the at least one FSD from becoming demodulated by respective carrier frequencies generated by the one or more additional FSDs in the FMS.

At 1310, the non-limiting method 1300 can comprise performing (e.g., by synchronization component 116), by the device, a pulse phase synchronization using a control system to prevent a signal transmitted by a first FSD of the FMS from entering a receive period of a second FSD of the FMS located directly across the first FSD at a distance, wherein the control system can measure an amount of harmonics generated by the first FSD at the second FSD and gradually shift a phase of the signal transmitted by the first FSD to align the signal transmitted by the first FSD with a signal transmitted by the second FSD in the FMS.

At 1312, the non-limiting method 1300 can determine (e.g., using synchronization component 116) whether the signal transmitted by the first FSD is phase shifted to align with the signal transmitted by the second FSD, by detecting and minimizing interaction frequencies, by identifying presence or absence of 1 kHz, 2 kHz, etc. harmonics.

If yes, at 1314, the non-limiting method 1300 can stop shifting the phase of the signal transmitted by the first FSD.

If no, at 1316, the non-limiting method 1300 can continue shifting the phase of the signal transmitted by the first FSD.

As stated elsewhere herein, crosstalk can be a common issue in fetal monitors that do not use TDM. Various embodiments herein can employ the same piezo crystals to electronically generate multiple carrier frequencies for transducers operating in FDM mode. Various embodiments herein can also employ specific separation of frequencies and use known interaction frequencies to eliminate cross talk in FMSs. Further, the embodiments discussed herein can perform PRR synchronizations and phase shifting to eliminate crosstalk between the transducers by detecting and minimizing interaction frequencies.

For simplicity of explanation, the computer-implemented and non-computer-implemented methodologies provided herein are depicted and/or described as a series of acts. It is to be understood that the subject innovation is not limited by the acts illustrated and/or by the order of acts, for example acts can occur in one or more orders and/or concurrently, and with other acts not presented and described herein. Furthermore, not all illustrated acts can be utilized to implement the computer-implemented and non-computer-implemented methodologies in accordance with the described subject matter. Additionally, the computer-implemented methodologies described hereinafter and throughout this specification are capable of being stored on an article of manufacture to enable transporting and transferring the computer-implemented methodologies to computers. The term article of manufacture, as used herein, is intended to encompass a computer program accessible from any computer-readable device or storage media.

The systems and/or devices have been (and/or will be further) described herein with respect to interaction between one or more components. Such systems and/or components can include those components or sub-components specified therein, one or more of the specified components and/or sub-components, and/or additional components. Sub-components can be implemented as components communicatively coupled to other components rather than included within parent components. One or more components and/or sub-components can be combined into a single component providing aggregate functionality. The components can interact with one or more other components not specifically described herein for the sake of brevity, but known by those of skill in the art.

One or more embodiments described herein can employ hardware and/or software to solve problems that are highly technical, that are not abstract, and that cannot be performed as a set of mental acts by a human. For example, a human, or even thousands of humans, cannot efficiently, accurately and/or effectively generate multiple different frequencies in a transducer of an FMS as the one or more embodiments described herein can enable this process. And, neither can the human mind nor a human with pen and paper implement pulse schemes and artifact elimination techniques for eliminating crosstalk for ultrasound coexistence in an FMS, as conducted by one or more embodiments described herein.

Figure 14:
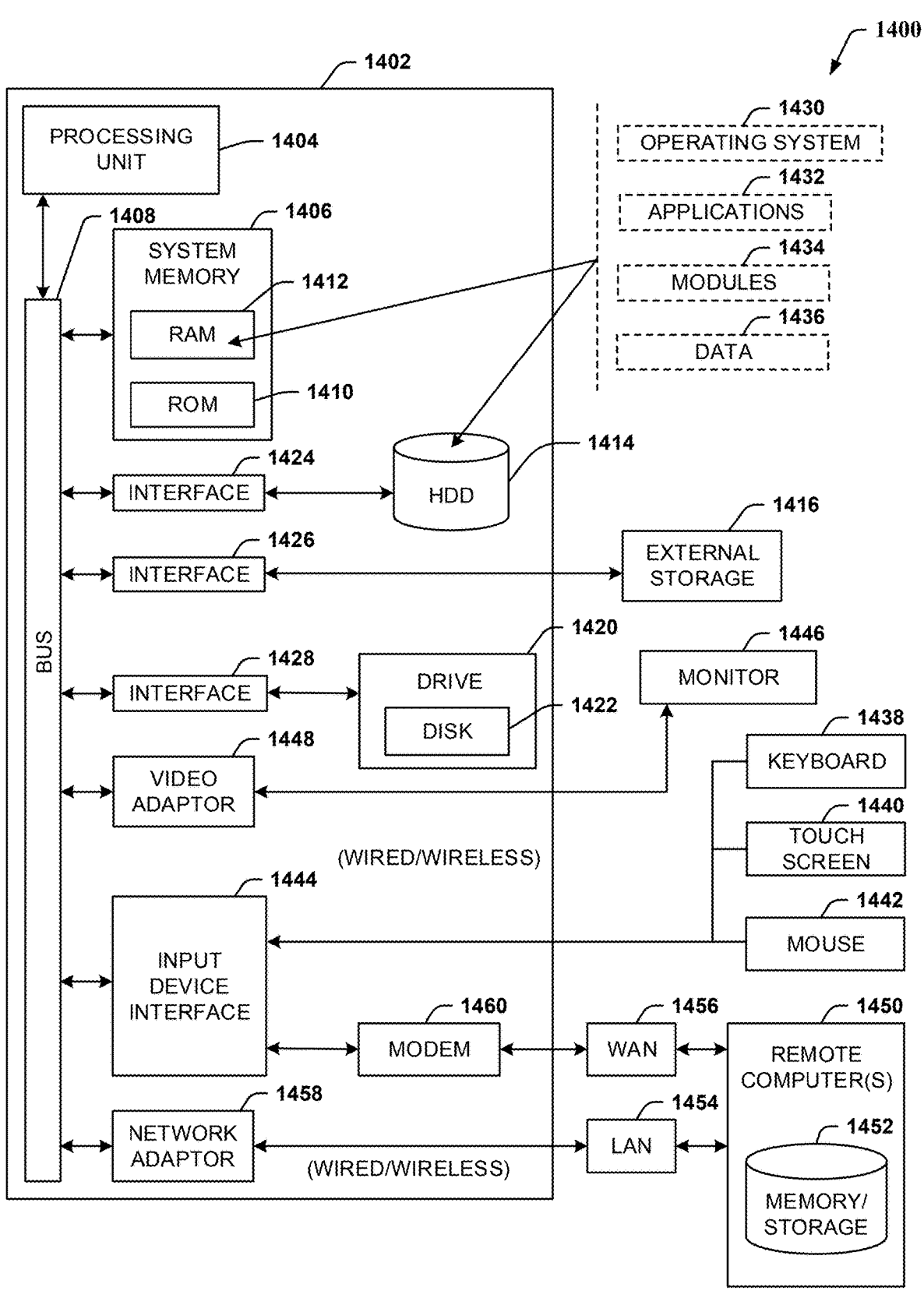
FIG. 14 illustrates a block diagram of an example, non-limiting operating environment in which one or more embodiments described herein can be facilitated.

In order to provide additional context for various embodiments described herein, FIG. 14 and the following discussion are intended to provide a brief, general description of a suitable computing environment 1400 in which the various embodiments described herein can be implemented. While the embodiments have been described above in the general context of computer-executable instructions that can run on one or more computers, those skilled in the art will recognize that the embodiments can be also implemented in combination with other program modules or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 14, the example environment 1400 for implementing various embodiments of the aspects described herein includes a computer 1402, the computer 1402 including a processing unit 1404, a system memory 1406 and a system bus 1408. The system bus 1408 couples system components including, but not limited to, the system memory 1406 to the processing unit 1404. The processing unit 1404 can be any of various commercially available processors. Dual microprocessors and other multi-processor architectures can also be employed as the processing unit 1404.

The system bus 1408 can be any of several types of bus structure that can further interconnect to a memory bus (with or without a memory controller), a peripheral bus, and a local bus using any of a variety of commercially available bus architectures. The system memory 1406 includes ROM 1410 and RAM 1412. A basic input/output system (BIOS) can be stored in a non-volatile memory such as ROM, erasable programmable read only memory (EPROM), EEPROM, which BIOS contains the basic routines that help to transfer information between elements within the computer 1402, such as during startup. The RAM 1412 can also include a high-speed RAM such as static RAM for caching data.

The computer 1302 further includes an internal hard disk drive (HDD) 1414 (e.g., EIDE, SATA), one or more external storage devices 1416 (e.g., a magnetic floppy disk drive (FDD) 1416, a memory stick or flash drive reader, a memory card reader, etc.) and a drive 1420, e.g., such as a solid state drive, an optical disk drive, which can read or write from a disk 1422, such as a CD-ROM disc, a DVD, a BD, etc. Alternatively, where a solid state drive is involved, disk 1422 would not be included, unless separate. While the internal HDD 1414 is illustrated as located within the computer 1402, the internal HDD 1414 can also be configured for external use in a suitable chassis (not shown). Additionally, while not shown in environment 1400, a solid state drive (SSD) could be used in addition to, or in place of, an HDD 1414. The HDD 1414, external storage device(s) 1416 and drive 1420 can be connected to the system bus 1408 by an HDD interface 1424, an external storage interface 1426 and a drive interface 1428, respectively. The interface 1424 for external drive implementations can include at least one or both of Universal Serial Bus (USB) and Institute of Electrical and Electronics Engineers (IEEE)

1394 interface technologies. Other external drive connection technologies are within contemplation of the embodiments described herein.

The drives and their associated computer-readable storage media provide nonvolatile storage of data, data structures, computer-executable instructions, and so forth. For the computer 1402, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1412, including an operating system 1430, one or more application programs 1332, other program modules 1434 and program data 1436. All or portions of the operating system, applications, modules, or data can also be cached in the RAM 1412. The systems and methods described herein can be implemented utilizing various commercially available operating systems or combinations of operating systems.

Computer 1402 can optionally comprise emulation technologies. For example, a hypervisor (not shown) or other intermediary can emulate a hardware environment for operating system 1430, and the emulated hardware can optionally be different from the hardware illustrated in FIG. 14. In such an embodiment, operating system 1430 can comprise one virtual machine (VM) of multiple VMs hosted at computer 1402. Furthermore, operating system 1430 can provide runtime environments, such as the Java runtime environment or the .NET framework, for applications 1432. Runtime environments are consistent execution environments that allow applications 1432 to run on any operating system that includes the runtime environment. Similarly, operating system 1430 can support containers, and applications 1432 can be in the form of containers, which are lightweight, standalone, executable packages of software that include, e.g., code, runtime, system tools, system libraries and settings for an application.

Further, computer 1402 can be enable with a security module, such as a trusted processing module (TPM). For instance with a TPM, boot components hash next in time boot components, and wait for a match of results to secured values, before loading a next boot component. This process can take place at any layer in the code execution stack of computer 1402, e.g., applied at the application execution level or at the OS kernel level, thereby enabling security at any level of code execution.

A user can enter commands and information into the computer 1402 through one or more wired/wireless input devices, e.g., a keyboard 1438, a touch screen 1440, and a pointing device, such as a mouse 1442. Other input devices (not shown) can include a microphone, an infrared (IR) remote control, a radio frequency (RF) remote control, or other remote control, a joystick, a virtual reality controller or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1404 through an input device interface 1444 that can be coupled to the system bus 1408, but can be connected by other interfaces, such as a parallel port, an IEEE 1394 serial port, a game port, a USB port, an IR interface, a BLUETOOTH® interface, etc.

A monitor 1446 or other type of display device can be also connected to the system bus 1308 via an interface, such as a video adapter 1448. In addition to the monitor 1446, a computer typically includes other peripheral output devices (not shown), such as speakers, printers, etc.

The computer 1402 can operate in a networked environment using logical connections via wired or wireless communications to one or more remote computers, such as a remote computer(s) 1450. The remote computer(s) 1450 can be a workstation, a server computer, a router, a personal computer, portable computer, microprocessor-based entertainment appliance, a peer device or other common network node, and typically includes many or all of the elements described relative to the computer 1402, although, for purposes of brevity, only a memory/storage device 1452 is illustrated. The logical connections depicted include wired/wireless connectivity to a local area network (LAN) 1454 or larger networks, e.g., a wide area network (WAN) 1456. Such LAN and WAN networking environments are commonplace in offices and companies, and facilitate enterprise-wide computer networks, such as intranets, all of which can connect to a global communications network, e.g., the Internet.

When used in a LAN networking environment, the computer 1402 can be connected to the local network 1454 through a wired or wireless communication network interface or adapter 1458. The adapter 1458 can facilitate wired or wireless communication to the LAN 1454, which can also include a wireless access point (AP) disposed thereon for communicating with the adapter 1458 in a wireless mode.

When used in a WAN networking environment, the computer 1402 can include a modem 1460 or can be connected to a communications server on the WAN 1456 via other means for establishing communications over the WAN 1456, such as by way of the Internet. The modem 1460, which can be internal or external and a wired or wireless device, can be connected to the system bus 1408 via the input device interface 1444. In a networked environment, program modules depicted relative to the computer 1402 or portions thereof, can be stored in the remote memory/storage device 1452. It will be appreciated that the network connections shown are example and other means of establishing a communications link between the computers can be used.

When used in either a LAN or WAN networking environment, the computer 1402 can access cloud storage systems or other network-based storage systems in addition to, or in place of, external storage devices 1416 as described above, such as but not limited to a network virtual machine providing one or more aspects of storage or processing of information. Generally, a connection between the computer 1402 and a cloud storage system can be established over a LAN 1454 or WAN 1456 e.g., by the adapter 1458 or modem 1460, respectively. Upon connecting the computer 1402 to an associated cloud storage system, the external storage interface 1426 can, with the aid of the adapter 1458 or modem 1460, manage storage provided by the cloud storage system as it would other types of external storage. For instance, the external storage interface 1426 can be configured to provide access to cloud storage sources as if those sources were physically connected to the computer 1402.

The computer 1402 can be operable to communicate with any wireless devices or entities operatively disposed in wireless communication, e.g., a printer, scanner, desktop or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

FIG. 15 is a schematic block diagram of a sample computing environment 1500 with which the disclosed subject matter can interact. The sample computing environment 1500 includes one or more client(s) 1510. The client(s) 1510 can be hardware or software (e.g., threads, processes, computing devices). The sample computing environment 1500 also includes one or more server(s) 1530. The server(s) 1530 can also be hardware or software (e.g., threads, processes, computing devices). The servers 1530 can house threads to perform transformations by employing one or more embodiments as described herein, for example. One possible communication between a client 1510 and a server 1530 can be in the form of a data packet adapted to be transmitted between two or more computer processes. The sample computing environment 1500 includes a communication framework 1550 that can be employed to facilitate communications between the client(s) 1510 and the server(s) 1530. The client(s) 1510 are operably connected to one or more client data store(s) 1520 that can be employed to store information local to the client(s) 1510. Similarly, the server(s) 1530 are operably connected to one or more server data store(s) 1540 that can be employed to store information local to the servers 1530.

Various embodiments may be a system, a method, an apparatus or a computer program product at any possible technical detail level of integration. The computer program product can include a computer readable storage medium (or media) having computer readable program instructions thereon for causing a processor to carry out aspects of various embodiments. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network or a wireless network. The network can comprise copper transmission cables, optical transmission fibers, wireless transmission, routers, firewalls, switches, gateway computers or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform various aspects.

Various aspects are described herein with reference to flowchart illustrations or block diagrams of methods, apparatus (systems), and computer program products according to various embodiments. It will be understood that each block of the flowchart illustrations or block diagrams, and combinations of blocks in the flowchart illustrations or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. These computer readable program instructions can also be stored in a computer readable storage medium that can direct a computer, a programmable data processing apparatus, or other devices to function in a particular manner, such that the computer readable storage medium having instructions stored therein comprises an article of manufacture including instructions which implement aspects of the function/act specified in the flowchart or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flow-chart or block diagram block or blocks.

The flowcharts and block diagrams in the Figures illustrate the architecture, functionality, and operation of possible implementations of systems, methods, and computer program products according to various embodiments. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer or computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that various aspects can be practiced with other computer system configurations, including single-processor or multi-processor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, or a computer. By way of illustration, both an application running on a server and the server can be a component. One or more components can reside within a process or thread of execution and a component can be localized on one computer or distributed between two or more computers. In another example, respective components can execute from various computer readable media having various data structures stored thereon. The components can communicate via local or remote processes such as in accordance with a signal having one or more data packets (e.g., data from one component interacting with another component in a local system, distributed system, or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. As used herein, the term "and/or" is intended to have the same meaning as "or." Moreover, articles "a" and "an" as used in the subject specification and annexed drawings should generally be construed to mean "one or more" unless specified otherwise or clear from context to be directed to a singular form. As used herein, the terms "example" or "exemplary" are utilized to mean serving as an example, instance, or illustration. For the avoidance of doubt, the subject matter disclosed herein is not limited by such examples. In addition, any aspect or design described herein as an "example" or "exemplary" is not necessarily to be construed as preferred or advantageous over other aspects or designs, nor is it meant to preclude equivalent exemplary structures and techniques known to those of ordinary skill in the art.

The herein disclosure describes non-limiting examples. For ease of description or explanation, various portions of the herein disclosure utilize the term "each," "every," or "all" when discussing various examples. Such usages of the term "each," "every," or "all" are non-limiting. In other words, when the herein disclosure provides a description that is applied to "each," "every," or "all" of some particular object or component, it should be understood that this is a non-limiting example, and it should be further understood that, in various other examples, it can be the case that such description applies to fewer than "each," "every," or "all" of that particular object or component.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer-executable components; and
a processor that executes the computer-executable components stored in the memory, wherein the computer-executable components comprise:
a synchronization component that performs a pulse phase synchronization using a control system to prevent a first signal transmitted by a first fetal sensor device (FSD) of a fetal monitoring system (FMS) from entering a receive period of a second FSD of the FMS located across the first FSD at a distance, wherein the control system measures an amount of harmonics generated by the first FSD at the second FSD and gradually shifts a phase of the first signal to align the first signal with a second signal transmitted by the second FSD in the FMS.

2. The system of claim 1, wherein the computer-executable components comprise:
a frequency generation component that uses a variable frequency generator circuitry to generate electronic signals at one or more different frequencies in at least one FSD of the FMS, wherein the at least one FSD dynamically adjusts a transmit voltage of the at least one FSD to maintain one acoustic power value at the one or more different frequencies, wherein the at least one FSD comprises a tunable inductor-capacitor (LC) tank circuit comprising capacitance varactors that tune a resonant frequency of the tunable LC tank circuit to a carrier frequency of the at least one FSD, wherein tuning the resonant frequency of the tunable LC tank circuit to the carrier frequency of the at least one FSD comprises using a digital-to-analog converter (DAC) to adjust biasing voltages of a varactor network, and wherein the carrier frequency is a frequency selected from the one or more different frequencies.

3. The system of claim 2, further comprising:
a storage component that stores a DAC value corresponding to maximizing gain of the tunable LC tank circuit at the carrier frequency of the at least one FSD.

4. The system of claim 2, wherein the variable frequency generator circuitry uses an attenuated shifted frequency to automate a calibration process for the tunable LC tank circuit, and wherein the at least one FSD is calibrated to maximize gain at the carrier frequency of the at least one FSD.

5. The system of claim 2, wherein based on tuning the resonant frequency of the tunable LC tank circuit to the carrier frequency of the at least one FSD, the tunable LC tank circuit maintains the resonant frequency within a predetermined tolerance range of the carrier frequency across a range of operating temperatures.

6. The system of claim 2, wherein, based on tuning the resonant frequency of the tunable LC tank circuit to the carrier frequency of the at least one FSD, the tunable LC tank circuit provides an amplitude response exhibiting maximum gain at the carrier frequency relative to adjacent frequencies, and attenuates signals at frequencies corresponding to carrier frequencies of additional FSDs in the FMS.

7. The system of claim 1, wherein the FMS comprises a plurality of FSDs, and wherein the computer-executable components further comprise:
a separation component that separates respective carrier frequencies of the plurality of FSDs in the FMS such that a frequency difference between carrier frequencies of any two FSDs is not a multiple of a pulse repetition rate (PRR) of either FSD, wherein separating the respective carrier frequencies of the plurality of FSDs generates predictable harmonics during crosstalk in the FMS.

8. The system of claim 7, further comprising:
a signal processing component that implements an automatic gain control stage and a filter to selectively eliminate the predictable harmonics to eliminate crosstalk in the FMS, wherein the automatic gain control stage is implemented as a software, a hardware or a combination of the software and the hardware.

9. The system of claim 1, wherein the FMS comprises a plurality of FSDs and wherein the synchronization component performs a periodic pulse repetition rate (PRR) synchronization to synchronize a start of a transmit period of at least one FSD of the FMS with respective starts of transmit periods of one or more additional FSDs in the FMS to prevent ultrasound signals generated by the at least one FSD from becoming demodulated by respective carrier frequencies generated by the one or more additional FSDs in the FMS.

10. The system of claim 9, wherein the periodic PRR synchronization is performed by using a monitor that sends signals in real time to FSDs of the FMS or by using a main FSD to transmit to additional FSDs in the FMS, and wherein the periodic PRR synchronization is performed wirelessly or through wired connections.

11. A computer-implemented method, comprising:
performing, by a device operatively coupled to a processor, a pulse phase synchronization using a control system to prevent a first signal transmitted by a first fetal sensor device (FSD) of a fetal monitoring system (FMS) from entering a receive period of a second FSD of the FMS located across the first FSD at a distance, wherein the control system measures an amount of harmonics generated by the first FSD at the second FSD and gradually shifts a phase of the first signal to align the first signal with a second signal transmitted by the second FSD in the FMS.

12. The computer-implemented method of claim 11, further comprising:
generating, by the device and using a variable frequency generator circuitry, electronic signals at one or more different frequencies in at least one FSD of the FMS, wherein the at least one FSD dynamically adjusts a transmit voltage of the at least one FSD to maintain one acoustic power value at the one or more different frequencies; and
tuning, by the device, a resonant frequency of a tunable LC tank circuit comprised in the at least one FSD to a carrier frequency of the at least one FSD, wherein the carrier frequency is a frequency selected from the one or more different frequencies, wherein the tunable LC tank circuit comprises capacitance varactors that perform the tuning, and wherein tuning the resonant frequency of the tunable LC tank circuit to the carrier frequency of the at least one FSD comprises using, by the device, a DAC to adjust biasing voltages of a varactor network to dynamically change a capacitance value of the capacitance varactors.

13. The computer-implemented method of claim 12, further comprising:
storing, by the device, a DAC value corresponding to maximizing gain of the tunable LC tank circuit at the carrier frequency of the at least one FSD.

14. The computer-implemented method of claim 12, further comprising:
using, by the device, an attenuated shifted frequency to automate a calibration process for the tunable LC tank circuit; and
calibrating, by the device, the at least one FSD to maximize gain at the carrier frequency of the at least one FSD.

15. The computer-implemented method of claim 12, wherein based on tuning the resonant frequency of the tunable LC tank circuit to the carrier frequency of the at least one FSD, the tunable LC tank circuit maintains the resonant frequency within a predetermined tolerance range of the carrier frequency across a range of operating temperatures.

16. The computer-implemented method of claim 11, wherein the FMS comprises a plurality of FSDs, and wherein the computer-implemented method further comprises:
separating, by the device, respective carrier frequencies of the plurality of FSDs in the FMS such that a frequency difference between carrier frequencies of any two FSDs is not a multiple of a PRR of either FSD, wherein separating the respective carrier frequencies of the plurality of FSDs generates predictable harmonics during crosstalk in the FMS; and
implementing, by the device, an automatic gain control stage and a filter to selectively eliminate the predictable harmonics to eliminate crosstalk in the FMS, wherein the automatic gain control stage is implemented as a software, a hardware or a combination of the software and the hardware.

17. The computer-implemented method of claim 11, wherein the FMS comprises a plurality of FSDs, and wherein the computer-implemented method further comprises:
performing, by the device, a periodic pulse repetition rate (PRR) synchronization to synchronize a start of a transmit period of at least one FSD of the FMS with respective starts of transmit periods of one or more additional FSDs in the FMS to prevent ultrasound signals generated by the at least one FSD from becoming demodulated by respective carrier frequencies generated by the one or more additional FSDs in the FMS.

18. The computer-implemented method of claim 17, wherein the periodic PRR synchronization is performed by using a monitor that sends signals in real time to FSDs of the FMS or by using a main FSD to transmit signals to additional FSDs in the FMS, and wherein the periodic PRR synchronization is performed wirelessly or through wired connections.

19. A non-transitory computer readable medium for ultrasound coexistence in a fetal monitoring system (FMS), the non-transitory computer readable medium comprising program instructions embodied therewith, the program instructions executable by a processor to cause the processor to:
perform a pulse phase synchronization using a control system to prevent a first signal transmitted by a first fetal sensor device (FSD) of the FMS from entering a receive period of a second FSD of the FMS located across the first FSD at a distance, wherein the control system measures an amount of harmonics generated by the first FSD at the second FSD and gradually shifts a phase of the first signal to align the first signal with a second signal transmitted by the second FSD in the FMS.

20. The non-transitory computer readable medium of claim 19, the program instructions executable by the processor to further cause the processor to:
generate, using a variable frequency generator circuitry, electronic signals at one or more different frequencies in at least one FSD of the FMS, wherein the at least one FSD dynamically adjusts a transmit voltage of the at least one FSD to maintain one acoustic power value at the one or more different frequencies; and
tune a resonant frequency of a tunable LC tank circuit comprised in the at least one FSD to a carrier frequency of the at least one FSD, wherein the carrier frequency is a frequency selected from the one or more different frequencies, wherein the tunable LC tank circuit comprises capacitance varactors that tune the resonant frequency, and wherein tuning the resonant frequency of the tunable LC tank circuit to the carrier frequency of the at least one FSD comprises using a DAC to adjust biasing voltages of a varactor network to dynamically change a capacitance value of the capacitance varactors.

* * * * *